United States Patent
Tadlock

(10) Patent No.: US 7,486,995 B2
(45) Date of Patent: Feb. 3, 2009

(54) SYSTEM AND METHOD FOR STIMULATION OF A PERSON'S BRAIN STEM

(75) Inventor: Charles H. Tadlock, Henderson, NV (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 430 days.

(21) Appl. No.: 11/316,648

(22) Filed: Dec. 20, 2005

(65) Prior Publication Data

US 2006/0136008 A1   Jun. 22, 2006

Related U.S. Application Data

(63) Continuation of application No. 10/750,788, filed on Jan. 2, 2004, now Pat. No. 6,978,180.

(51) Int. Cl.
*A61N 1/05*   (2006.01)

(52) U.S. Cl. ..................................... 607/116

(58) Field of Classification Search ............. 607/39–58, 607/115–156
See application file for complete search history.

(56) References Cited

U.S. PATENT DOCUMENTS

| | | | | |
|---|---|---|---|---|
| 4,869,255 A | 9/1989 | Putz | ............................ | 128/642 |
| 5,121,754 A | 6/1992 | Mullett | ......................... | 128/786 |
| 6,263,225 B1 | 7/2001 | Howard, III | ................. | 600/378 |
| 6,356,784 B1 | 3/2002 | Lozano et al. | .................. | 607/2 |
| 7,155,284 B1 * | 12/2006 | Whitehurst et al. | ........... | 607/44 |
| 2004/0243206 A1 | 12/2004 | Tadlock | | |
| 2004/0249428 A1 | 12/2004 | Tadlock | | |

OTHER PUBLICATIONS

Tadlock, "System and Method of Stimulation of a Person's Brain Stem," U.S. Appl. No. 10/750,788, 58 pages, pending, filed Jan. 2, 2004.

PCT, Notification of Transmittal of the International Search Report and the Written Opinion of the International Searching Authority, or the Declaration, PCT/US04/00030, 7 pages, Dated: Jan. 2, 2004 Mailed Nov. 30, 2004.

* cited by examiner

*Primary Examiner*—Scott M Getzow
(74) *Attorney, Agent, or Firm*—Christopher S. L. Crawford; Peter Lando; Melissa Acosta

(57) ABSTRACT

According to one embodiment, a neurological stimulation system includes an electrical stimulation lead suited for implantation into the epidural space overlying the medulla for stimulation of nerve tissue in the brain stem. The lead includes a plurality of electrodes suited to be positioned in the epidural space overlying the medulla and to deliver stimulation energy to the nerve tissue. The system also includes a stimulation source suited for implantation into the person's body and operable to generate signals for transmission to the electrodes of the lead positioned in the epidural space overlying the medulla to cause the electrodes to deliver stimulation energy to the nerve tissue. In a particular embodiment, the lead may be suited for implantation posteriorly on, in, or near the brain stem overlying the medulla. In a particular embodiment, the lead may be inserted through an open craniotomy or a burr hole located approximately over the junction of the occiput and the first or second cervical vertebrae.

8 Claims, 17 Drawing Sheets

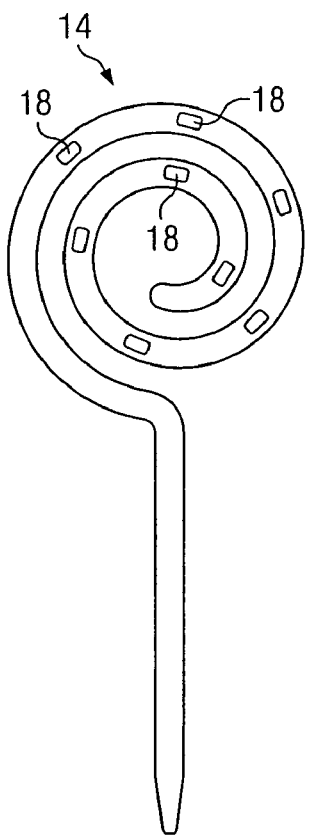 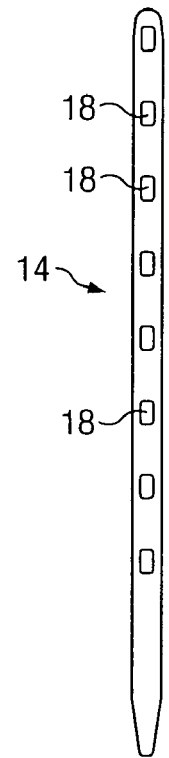
FIG. 13A    FIG. 13B
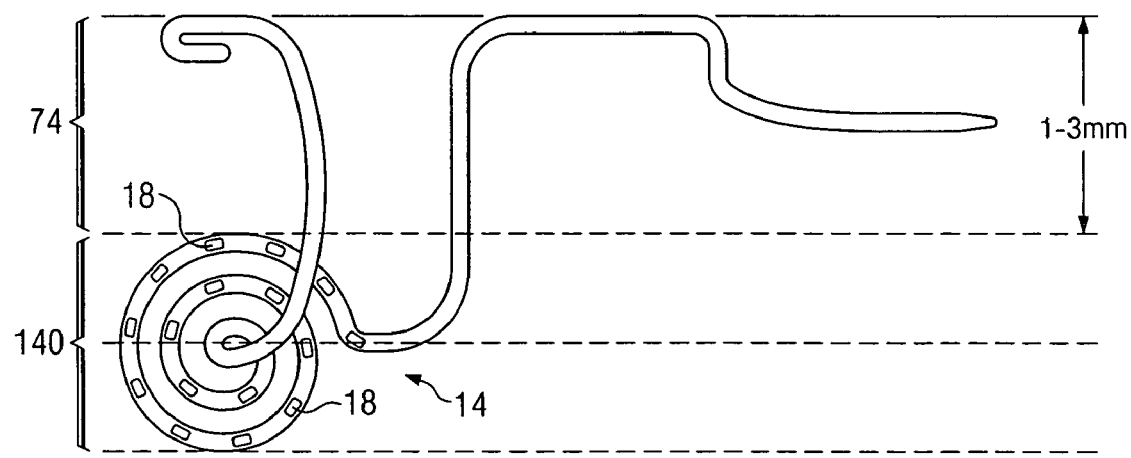
FIG. 14

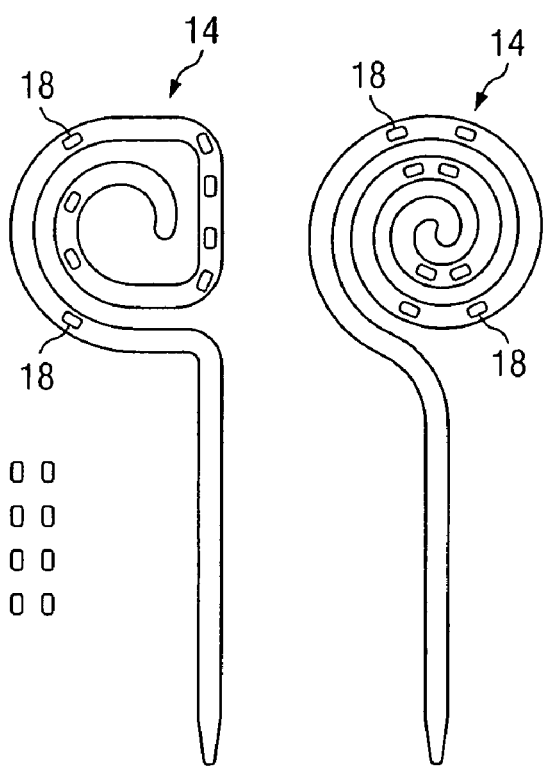
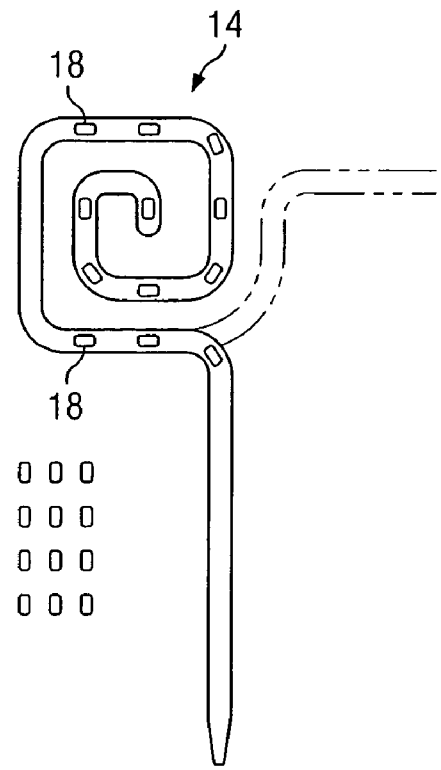
FIG. 22A  FIG. 22B
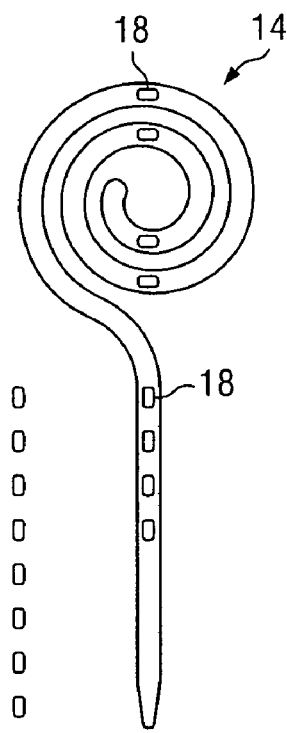
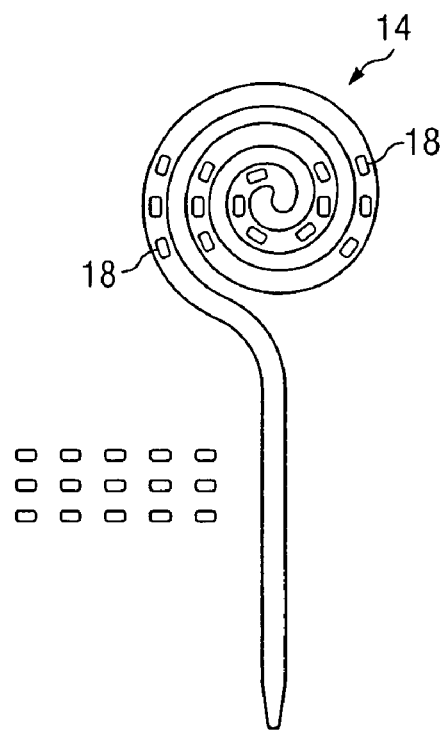
FIG. 22C  FIG. 22D

SYSTEM AND METHOD FOR STIMULATION OF A PERSON'S BRAIN STEM

RELATED APPLICATIONS

This application is a continuation of U.S. application Ser. No. 10/750,788, filed Jan. 2, 2004, now U.S. Pat. No. 6,978, 180. This application is also related to U.S. application Ser. No. 10/835,108, filed Apr. 28, 2004, currently pending, and U.S. application Ser. No. 10/834,743, filed Apr. 28, 2004, currently pending.

TECHNICAL FIELD

The present invention relates generally to neurological stimulation including infusion for medical applications and in particular to a system and method for stimulation of a person's brain stem.

BACKGROUND

Stimulation may be applied to target nerve tissue in the brain or spinal cord to treat a variety of clinical conditions. According to one technique, a set of efficacious neurological stimulation parameters are determined, the set of parameters is entered into the system, and the system is used to stimulate, either electrically or chemically, the target nerve tissue according to the set of parameters to treat a condition.

For electrical stimulation, typically, an implanted pulse generator (IPG) transmits a pulse of efficacious electrical energy to an implanted electrical stimulation lead according to the set of parameters and, in response to the pulse, the electrodes of the implanted stimulation lead deliver the electrical energy to the target nerve tissue to treat the condition. For chemical stimulation, typically, an implantable drug pump transmits a pulse of efficacious drugs through a catheter according to the set of parameters and, in response to the pulse, infusion ports of the implanted catheter deliver the chemical dose to the target nerve tissue to treat the condition.

However, there exists a certain population of patients with conditions that are intractable to standard therapies. For example, some patients with neurodegenerative diseases or trauma such as cerebral infarct or spinal cord injury may experience pain or undesirable movements such as spasticity or dyskinesia that are not responsive to stimulation of the cortex or spinal cord. As another example, some patients with chronic pain in multiple locations may not obtain full relief using previous stimulation techniques. Alternative stimulation methods are desirable to treat the population of patients with conditions that are intractable to standard therapies.

SUMMARY OF THE INVENTION

The neurological stimulation system and the associated electrical stimulation leads, infusion catheters, and methods of the present invention may reduce or eliminate certain problems and disadvantages associated with prior techniques for stimulating the brain or spinal cord.

According to one embodiment, a neurological stimulation system is suited for electrical stimulation of target nerve tissue in the person's brain stem. The system includes an electrical stimulation lead suited for implantation into the epidural space overlying the medulla for electrical stimulation of target nerve tissue in the brain stem. The lead includes a plurality of electrodes suited to be positioned in the epidural space overlying the medulla and to deliver electrical stimulation energy to the target nerve tissue in the brain stem. The system also includes a stimulation source suited for implantation into the person's body and operable to generate signals for transmission to the electrodes of the lead positioned in the epidural space overlying the medulla to cause the electrodes to deliver electrical stimulation energy to the target nerve tissue in the brain stem.

According to another embodiment, a method is provided for neurological stimulation of target nerve tissue in a person's brain stem. The method includes implanting an electrical stimulation lead into the epidural space overlying the medulla, the lead comprising a plurality of electrodes suited to be positioned in the epidural space overlying the medulla and to deliver electrical stimulation energy to the target nerve tissue in the brain stem. The method also includes implanting a stimulation source into the person's body, the stimulation source operable to generate signals for transmission to the electrodes of the lead positioned in the epidural space overlying the medulla to cause the electrodes to deliver electrical stimulation energy to the target nerve tissue in the brain stem. The method further includes, in response to the signals transmitted from the stimulation source, using the electrodes of the lead positioned in the epidural space overlying the medulla to deliver electrical stimulation energy to the target nerve tissue in the brain stem.

According to another embodiment, a method is provided for electrical stimulation of target nerve tissue in a person's brain stem. The method includes selecting an electrical stimulation lead suited for implantation posteriorly on, in, or near the brain stem overlying the medulla for electrical stimulation of target nerve tissue in the brain stem, the lead comprising a plurality of electrodes suited to be positioned posteriorly on, in, or near the brain stem overlying the medulla and to deliver electrical stimulation energy to the target nerve tissue in the brain stem. The method also includes creating an opening in the person's skull overlying the medulla, inserting the lead through the opening in the skull overlying the medulla, and positioning the lead posteriorly on, in, or near the brain stem overlying the medulla for electrical stimulation of the target nerve tissue in the brain stem.

Particular embodiments of the present invention may provide one or more technical advantages. For example, in certain embodiments, stimulating in the brain stem makes it possible to stimulate multiple nerve pathways, associated with areas of the deep brain or the spinal cord for example, using an electrical stimulation lead or infusion catheter implanted in or near the brain stem rather than requiring the lead or catheter to be implanted proximate these areas of the deep brain or spinal cord. Certain embodiments allow the electrical stimulation lead or infusion catheter to be implanted using any number of techniques, such as percutaneous insertion, insertion through an open craniotomy, or insertion through a burr hole formed in the skull. Certain embodiments provide electrical stimulation leads or infusion catheters configured for optimal performance and stability when implanted on, in, or near the brain stem. For example, certain embodiments may use a resilient spiral matrix lead having a spiral natural position, adapted to be straightened for insertion through an introducer to a desired position on, in, or near the brain stem, and adapted to curl into its spiral natural position to allow stimulation of a broader area than would be possible using a conventional "in-line" lead and also to press against surrounding tissue after insertion to stabilize and maintain the lead in its desired position. As another example, certain embodiments may use a resilient sheet matrix lead having a sheet-like natural position, adapted to be rolled upon itself similar to a scroll for insertion through an introducer to a desired position on, in, or near the brain stem, and adapted to unroll to its sheet-like natural position after insertion for stimulation of a broader area than would be possible using a conventional "in-line" lead. Certain embodiments allow a medication or other chemical to be delivered to target nerve tissue in the brain stem using an implanted infusion pump and catheter for chemical stimulation of the target nerve tissue in the brain stem, in conjunction with or independent from any electrical stimulation of the target nerve tissue in the brain stem.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

For a more complete understanding of the present invention and features and advantages thereof, reference is now made to the following description taken in conjunction with the accompanying drawings, in which:

FIGS. 13A-13B illustrate an example spiral matrix electrical stimulation lead;

FIG. 14 illustrates an example spiral matrix electrical stimulation lead situated in the dural layer of the brain stem;

FIGS. 22A-22D illustrate example spiral matrix leads;

DESCRIPTION OF EXAMPLE EMBODIMENTS

Figure 1A:
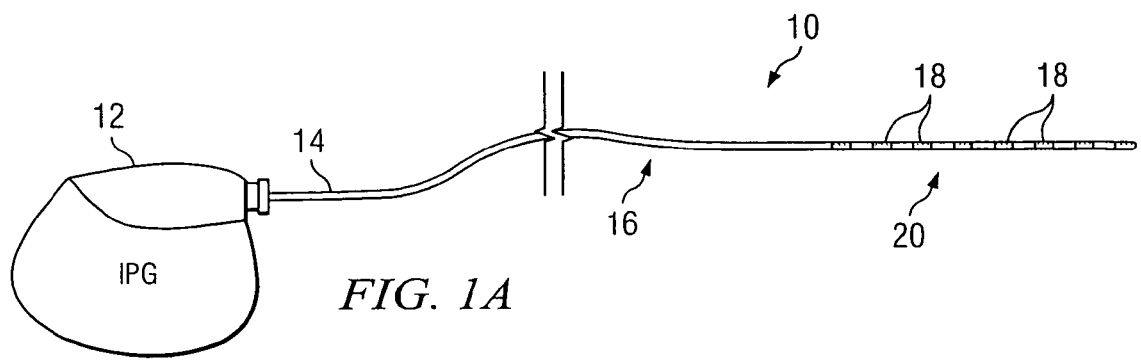
FIGS. 1A-1B illustrate example electrical stimulation systems for implantation into a person's body for electrical stimulation of target nerve tissue in the brain stem.

The present invention provides a system and method for stimulating a person's brain stem to treat various neurological disorders such as pain. The brain stem is the stem-like portion of the brain that connects the cerebral hemispheres with the spinal cord and includes the medulla oblongata, the pons, and the midbrain. Because the brain stem connects the brain with the spinal cord, it serves as the main router for the central nervous system (CNS). This anatomic arrangement allows for the stimulation of all major nerve tracts and nuclei within a defined, compact area. Stimulating in the brain stem region also provides the ability to stimulate deep brain centers via both antegrade and retrograde conduction. Thus, both nerve tissue in the spinal cord and nerve centers in the brain may be stimulated from the brain stem region.

Stimulation of the brain stem provides a site for stimulation and hence pain relief for various parts of the body, notably areas such as the head and face, the meninges, and the intracranial vessels and associated nerve innervation that would otherwise be difficult to access for stimulation. In certain embodiments, the present invention provides for stimulation that treats patients with intractable headache and head and neck pain. Furthermore, in certain embodiments, brain stem stimulation allows the entire body or a substantial portion of it to be stimulated from one location. Hence, pain throughout the body may be treated from one location. For example, a patient with diabetic peripheral neuropathy, having pain in the hands and feet in a "glove" or "stocking" distribution, respectively, may be treated using a single IPG and one or more electrical stimulation leads implanted on, in, or near the brain stem. In certain embodiments, the present invention allows multiple sites to be stimulated using a single unilateral electrical stimulation lead implanted at one location on, in, or near the brain stem. For example, such multiple sites may include both hands and both feet, multiple sites in both the back and neck, or any other suitable combination of sites. As another example, for patients with peripheral vascular disease present in the upper and lower extremities, certain embodiments may provide pain relief and improve blood flow to multiple sites throughout the body by stimulating a single site in the brain stem. The present invention contemplates stimulating target nerve tissue in the brain stem for treatment of pain in any region of the body according to particular needs and circumstances.

In certain embodiments, stimulation of the brain stem may provide a method for treating depression and seizures. In addition, certain embodiments may provide a method for treating cardiac disease, such as heart failure, arrhythmias, or cardiac pain for example, through vagal nerve stimulation. Furthermore, in certain embodiments, cardiac accelerator and decelerator nerves identified within the brain stem may be electrically stimulated.

In certain embodiments, stimulation of the brain stem allows for precise targeting of specific sites. For example, specific nuclei (such as the dorsal motor nucleus of the vagus), specific neural cell clusters, and the entry zone of the vagus may be stimulated. As another example, the nucleus solitarius that controls ventilation and taste may be stimulated. As another example; the expiratory and inspiratory centers in the medulla oblongata and the olivary nuclei, cerebellar tracts (the olivocerebellar tract, and dorsal spinocerebellar tract) that control spasticity and motor control may be stimulated. As another example, the inferior cerebellar peduncle and extrapyramidal system, accessible via cerebellar tracts, and other sites that affect the symptoms of Parkinson's disease, vestibular disease, and tremor may be stimulated. As another example, corticospinal tracts either for direct pyramidal control (to treat movement disorders) or for stimulation of a portion of the pyramidal tract, thought to represent descending inhibition of lower spinal centers, may be stimulated to control spasticity. As another example, other nuclei, such as the nuclei that control nausea, may be stimulated. The present invention contemplates precise targeting of any specific site according to particular needs and circumstances.

In certain embodiments, the present invention also provides for stimulation of the brain stem by direct, targeted infusion of medications or other chemical directly into a specific area of the brain stem. Direct epidural infusion of local anesthetic at low doses may provide total body analgesia. Therefore, in certain embodiments, previously untreatable patients with intractable pain, from thalamic pain syndrome for example, may now be treated. Also, in certain embodiments, continuous infusion of local anesthetics may enable intubated patients (patients on ventilators) to be kept comfortable while administering only minimal medications. Additionally, in certain embodiments, by administering only minimal medications, the medications may be readily and quickly reversed when the intubated patient is ready for unassisted ventilation. Furthermore, in certain embodiments, such treatment may be achieved using relatively inexpensive local anesthetics or combinations of local anesthetics, narcotics, or other centrally active drugs (e.g., clonidine or dexmeditomidine) that are delivered, for example, from an implantable medical device such as a drug pump through a catheter. Higher concentrations of these medications are currently used to induce general anesthesia. In certain embodiments, by providing a method of infusing only small amounts of these medications to targeted areas in the brain stem, these medications can be utilized for purposes other than general anesthesia.

In certain embodiments, infusion of low doses of narcotics or local anesthetics directly into the brain stem and contained in the dural barrier at the foramen magnum enables the implantation of totally implantable epidural pumps. The use of implanted epidural pumps has been limited because the medications infused into the epidural space may spread throughout the body. By using an epidural pump targeted to a site in the brain stem, smaller doses of medications may be used thereby alleviating the concern for toxicity associated with using larger doses of medications. A variety of biologically active substances may be infused, for example, neurotrophic substances stimulating nerve growth or regeneration.

Certain embodiments provide combination electrical stimulation leads and infusion catheters that offer improved pain control to patients with chronic pain and other conditions. The use of electrical stimulation in combination with epidurally-infused local anesthetics and narcotic medications, immediately after surgery for example, may significantly reduce a patient's pain and decrease the incidence of chronic pain. Combination electrical stimulation leads and infusion catheters on, in, or near the brain stem may be used to control pain in cardiac patients, for example, to relieve angina and improve coronary perfusion.

Figure 1B:
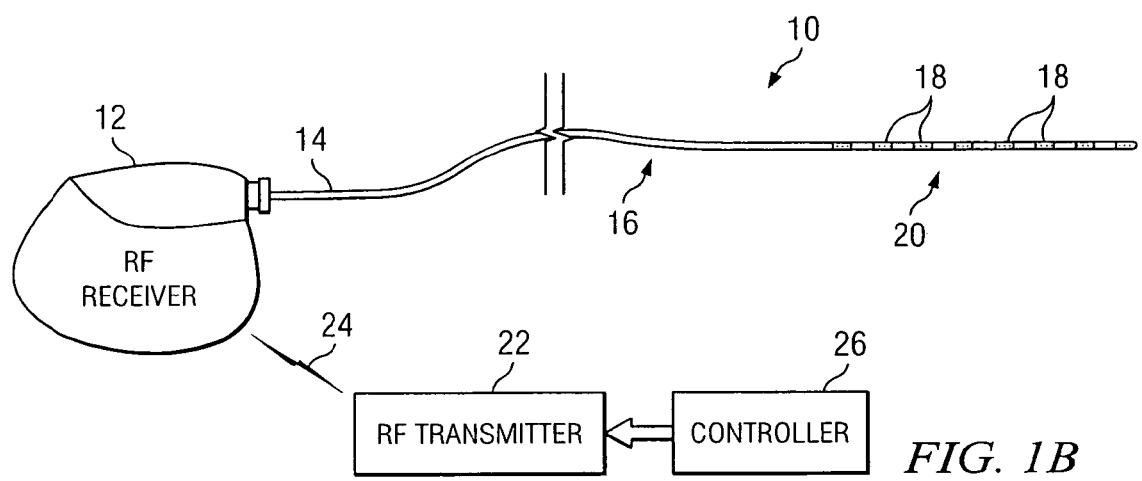

FIGS. 1A-1B illustrate example electrical stimulation systems 10 for implantation into a person's body for electrical stimulation of target nerve tissue in the brain stem. Such stimulation may be used to treat various neurological disorders such as pain. Stimulation system 10 generates and applies a stimulus to a target area of the brain stem. In general terms, stimulation system 10 includes an implantable electrical stimulation source 12 and an implantable electrical stimulation lead 14 for applying the stimulation signal to the target brain tissue. In operation, both of these primary components are implanted in the person's body, as discussed below with reference to FIG. 3A. Stimulation source 12 is coupled to a connecting portion 16 of electrical stimulation lead 14. Stimulation source 12 controls the electrical signals transmitted to one or more electrodes 18 located on a stimulating portion 20 of electrical stimulation lead 14, which is located on, in, or near the target brain tissue, according to suitable signal parameters (e.g., duration, intensity, frequency, etc.). A doctor, the patient, or another user of stimulation source 12 may directly or indirectly input signal parameters into stimulation source 12 for controlling the nature of the electrical stimulation provided.

In one embodiment, as shown in FIG. 1A, stimulation source 12 includes an IPG. An example IPG may be one manufactured by Advanced Neuromodulation Systems, Inc., such as the Genesis® System, part numbers 3604, 3608, 3609, and 3644. In another embodiment, as shown in FIG. 1B, stimulation source 12 includes an implantable wireless receiver. An example wireless receiver may be one manufactured by Advanced Neuromodulation Systems, Inc., such as the Renew® System, part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides control signals to wireless transmitter 22, wireless transmitter 22 transmits the control signals and power to the wireless receiver of stimulation source 12, and stimulation source 12 uses the control signals to vary the parameters of the electrical pulse transmitted through electrical stimulation lead 14 to the stimulation site. An example wireless transmitter 122 may be one manufactured by Advanced Neuromodulation Systems, Inc., such as the Renew® System, part numbers 3508 and 3516.

FIGS. 2A-2I illustrate example electrical stimulation leads 14 that may be used for implantation into a person's body for electrical stimulation of target nerve tissue in the brain stem. Such stimulation may be used to treat various neurological disorders such as pain. As described above, each of the one or more leads 14 incorporated in stimulation system 10 includes one or more electrodes 18 adapted to be positioned near the target brain tissue and used to deliver electrical stimulation energy to the target brain tissue in response to electrical signals received from stimulation source 12. A percutaneous lead 14, such as example leads 14a-d, may include one or more circumferential electrodes 18 spaced apart from one another along the length of lead 14. Circumferential electrodes 18 emit electrical stimulation energy generally radially in all directions and may be inserted percutaneously or through a needle. The electrodes 18 of a percutaneous lead 14 may be arranged in configurations other than circumferentially, for example as in a "coated" lead 14. A laminotomy or paddle style lead 14, such as example leads 14e-i, includes one or more directional electrodes 18 spaced apart from one another along one surface of lead 14. Directional electrodes 18 emit electrical stimulation energy in a direction generally perpendicular to the surface of lead 14 on which they are located. Although various types of leads 14 are shown as examples, the present invention contemplates stimulation system 10 including any suitable type of lead 14 in any suitable number, including three-dimensional leads and matrix leads as described below. In addition, the leads may be used alone or in combination. For example, unilateral stimulation of the brain is typically accomplished using a single lead 14 implanted in one side of the brain, while bilateral stimulation of the brain is typically accomplished using two leads 14 implanted in opposite sides of the brain.

Figure 3A:
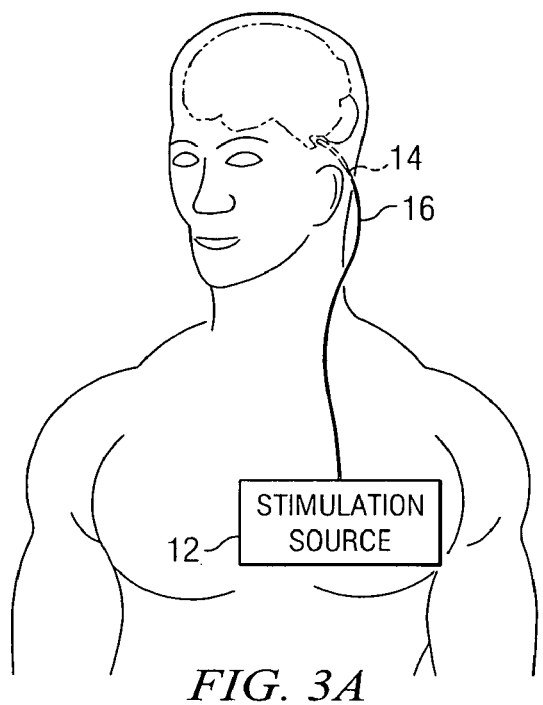
FIG. 3A illustrates example placement of the electrical stimulation system shown in FIGS. 1A-1B within a person's body.

FIG. 3A illustrates example placement of the electrical stimulation system 10 shown in FIGS. 1A-1B within a person's body. Electrical stimulation lead 14 is implanted on, in, or near target nerve tissue in brain stem. In certain embodiments, electrical stimulation lead 14 is located at least partially within or below the dura mater adjacent the brain stem. Stimulation source 12 may be implanted within a subcutaneous pocket formed in the person's torso (such as in the chest or buttocks), and connecting portion 16 tunneled, at least in part, subcutaneously (i.e. underneath the person's skin) to connect stimulation source 12 with electrical stimulation lead 14. However, stimulation source 12 may be located at any suitable location within the person's body according to particular needs.

Figure 3B:
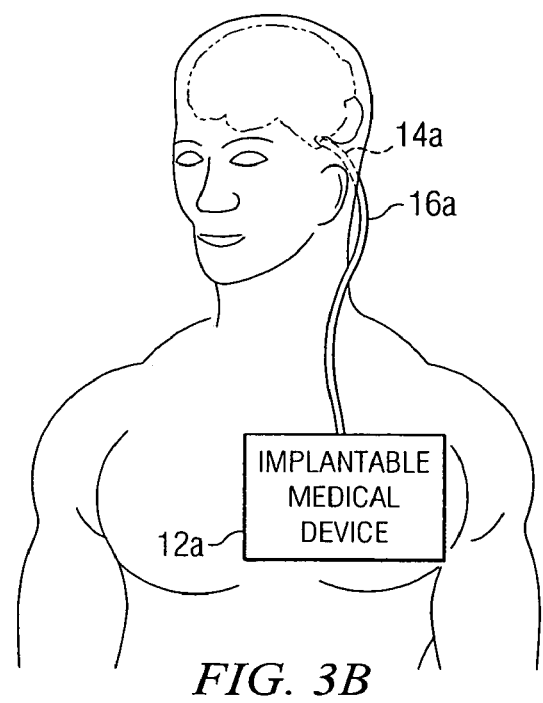
FIG. 3B illustrates example placement of an implantable medical device for neurological stimulation of target nerve tissue in the brain stem.

FIG. 3B illustrates example placement of an implantable medical device 12a for neurological stimulation of target nerve tissue in the brain stem. For example, as discussed above, a neurological stimulation system may include an implantable medical device 12a for the delivery of medications to target nerve tissue in the brain stem. Catheter tip 14a is implanted on, in, or near target nerve tissue in the brain stem. In certain embodiments, catheter tip 14a is located at least partially within or below the dura mater adjacent the brain stem. Implantable medical device 12a, for example, a medication infusion pump 12a, may be implanted within a subcutaneous pocket formed in the person's torso (such as in the chest or buttocks), and catheter 16a tunneled, at least in part, subcutaneously (i.e. underneath the person's skin. However, infusion pump 12a may be located at any suitable location within the person's body according to particular needs. In certain embodiments, appropriate infusion pumps 12a may include those illustrated and described in U.S. Pat. Nos. 4,772,263 and 6,666,845, which are hereby incorporated by reference herein as if fully illustrated and described herein.

Figure 4:
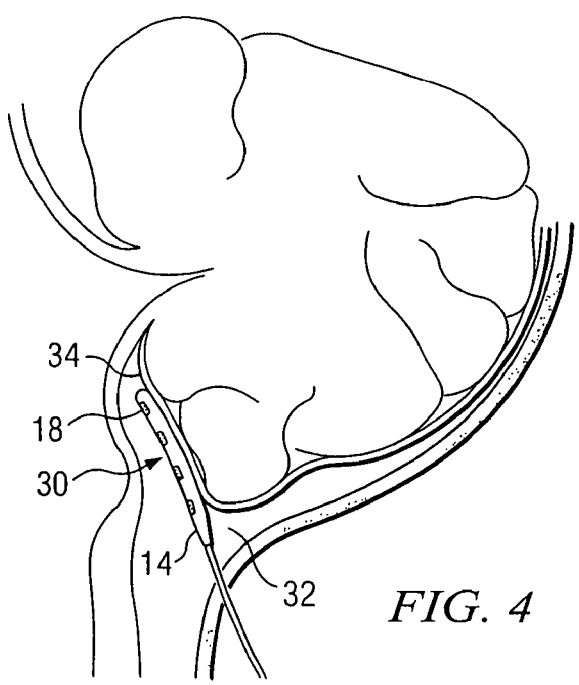
FIG. 4 is a cross-section of a portion of a person's head illustrating an example location of an electrical stimulation lead for electrical stimulation of target nerve tissue in the brain stem.

FIG. 4 is a cross-section of a portion of the person's head illustrating an example location of electrical stimulation lead 14 for electrical stimulation of target nerve tissue in the brain stem 30. In certain embodiments, as discussed above, electrical stimulation lead 14 is located in the extradural region 32 outside the dura mater 34 adjacent the brain stem 30. In FIG. 4, stimulation lead electrodes are directed towards the specific area of the brain stem 30 in which electrical stimulation is desired. In other embodiments, electrical stimulation lead 14 could be replaced with infusion catheter 14a, or a combined electrical stimulation lead and infusion catheter such as are described in FIGS. 21A-21B, depending on the type of stimulation desired at the targeted site.

Figure 5:
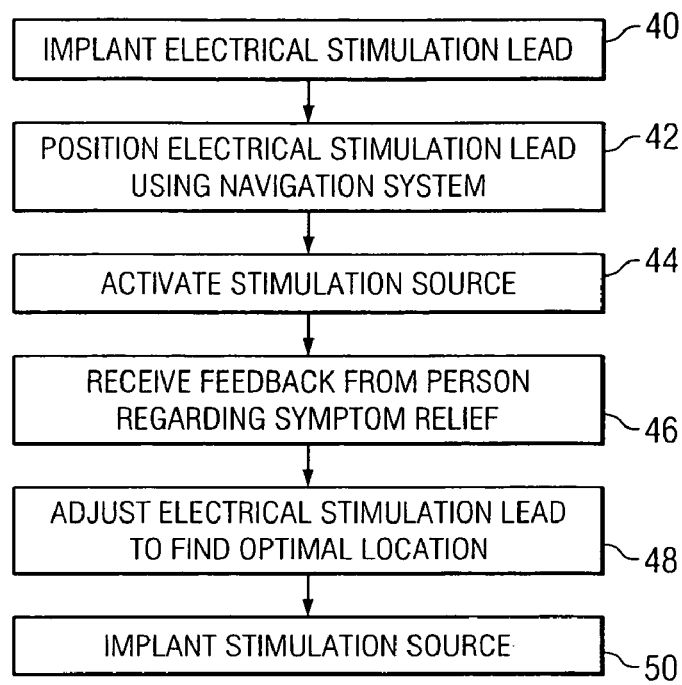
FIG. 5 illustrates steps of an example method for determining the location for an electrical stimulation lead and implanting the electrical stimulation system of FIGS. 1A-1B into a person's body.

FIG. 5 illustrates steps of an example method for determining the location for electrical stimulation lead 14 and implanting the electrical stimulation system 10 of FIGS. 1A-1B into a person's body. At step 40, an electrical stimulation lead is implanted on, in, or near the brain stem by accessing the brain tissue through a percutaneous route, an open craniotomy, or a burr hole. Where a burr hole is the means of accessing the brain stem, for example, stereotactic equipment suitable to aid in placement of an electrical stimulation lead 14 on, in, or near the brain stem may be positioned around the head. Then, an insertion cannula or introducer for electrical stimulation lead 14 may be inserted through the burr hole into the brain at step 40, but a cannula is not typically used where lead 14 is a laminotomy or paddle style lead 14. A cannula and electrical stimulation lead 14 may be inserted together or lead 14 may be inserted through the cannula after the cannula has been inserted. Guided by the navigation system with any necessary data obtained from previous imaging or other tests, electrical stimulation lead 14 is precisely positioned on, in, or near the brain stem at step 42 such that one or more electrodes 18 are located on, in, or near target nerve tissue in the brain stem. In certain embodiments, electrical stimulation lead 14 may be positioned extradurally.

Once electrical stimulation lead 14 has been properly positioned on, in, or near the targeted brain tissue, such that the targeted nucleus or other area of stimulation has been contacted for example, lead 14 is uncoupled from any stereotactic equipment that may have been used, and any cannula and stereotactic equipment are removed. Where stereotactic equipment is used, any cannula may be removed before, during, or after removal of the stereotactic equipment.

Once electrical stimulation lead 14 has been inserted and secured the patient might undergo a trial stimulation period at steps 44 through 48, which is familiar to those skilled in the art. With or without a trial stimulation period, stimulation source 12 may be implanted in the person's body at step 50 if permanent implantation is desired. The implant site is typically a subcutaneous pocket formed to receive and house stimulation source 12. The implant site is usually positioned a distance away from the insertion site, such as in the chest, buttocks, or another suitable location. However, a suitably small stimulation source 12 may be used to allow stimulation source 12 to be implanted at or near the stimulation site, for example, on, in, or near the brain stem. Connecting portion 16 of lead 14 extends from the lead insertion site to the implant site at which stimulation source 12 is implanted. Those skilled in the art will recognize that an extension might be used to connect electrical stimulation lead 14 to stimulation source 12 if required. A doctor, the patient, or another user of stimulation source 12 may directly or indirectly input appropriate signal parameters for the stimulation therapy to specify the nature of the stimulation provided. The same or analogous steps may be used for the implantation of a system for chemical stimulation of the brain stem, as described above with reference to FIG. 3B, substituting an infusion pump 12a for stimulation source 12 and an infusion catheter 14a for electrical stimulation lead 14.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting an example stimulation system 10 into a person for electrical stimulation of the person's brain stem.

Figure 6:
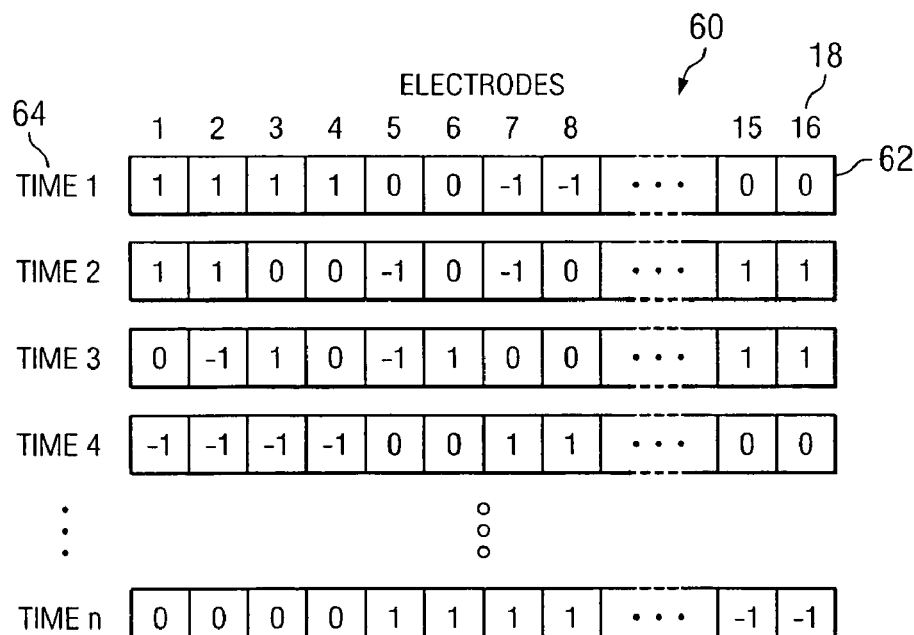
FIG. 6 illustrates an example stimulation set.

FIG. 6 illustrates an example stimulation set 60. One or more stimulation sets 60 may be provided, each stimulation set 60 specifying a number of stimulation parameters for the stimulation set 60. For example, as described more fully below with reference to FIGS. 7-8, multiple stimulation sets 60 may be executed in a suitable sequence according to a pre-programmed or randomized stimulation program. Example stimulation parameters for a stimulation set 60 may include an amplitude, a frequency, phase information, and a pulse width for each of a series of stimulation pulses that electrodes 18 are to deliver to the target brain tissue during a time interval during which stimulation set 60 is executed, along with a polarity 62 for each electrode 18 within each stimulation pulse. Stimulation parameters may also include a pulse shape, for example, biphasic cathode first, biphasic anode first, or any other suitable pulse shape. Stimulation parameters are not limited to the preceding but may include any suitable parameters known to those skilled in the art.

The polarity for an electrode 18 at a time 64 beginning a corresponding stimulation pulse or sub-interval within a stimulation pulse may be a relatively positive polarity 62, a relatively negative polarity 62, or an intermediate polarity 62 between the relatively positive polarity 62 and relatively negative polarity 62. For example, the relatively positive polarity 62 may involve a positive voltage, the relatively negative polarity 62 may involve a negative voltage, and the relatively intermediate polarity 62 may involve a zero voltage (i.e. "high impedance"). As another example, the relatively positive polarity 62 may involve a first negative voltage, the relatively negative polarity 62 may involve a second negative voltage more negative than the first negative voltage, and the relatively intermediate polarity 62 may involve a negative voltage between the first and second negative voltages. The availability of three distinct polarities 62 for an electrode 18 may be referred to as "tri-state" electrode operation. The polarity 62 for each electrode 18 may change for each of the sequence of times 64 corresponding to stimulation pulses or to sub-intervals within a stimulation pulse according to the stimulation parameters specified for the stimulation set 60. For example, as is illustrated in FIG. 6 for an example stimulation set 60 for a lead 14 with sixteen electrodes 18, the polarities 62 of the sixteen electrodes 18 may change for each of the sequence of times 64. In the example of FIG. 6, a relatively positive polarity 62 is represented using a "1," a relatively intermediate polarity 62 is represented using a "0," and a relatively negative polarity 62 is represented using a "−1," although any values or other representations may be used.

Figure 8:
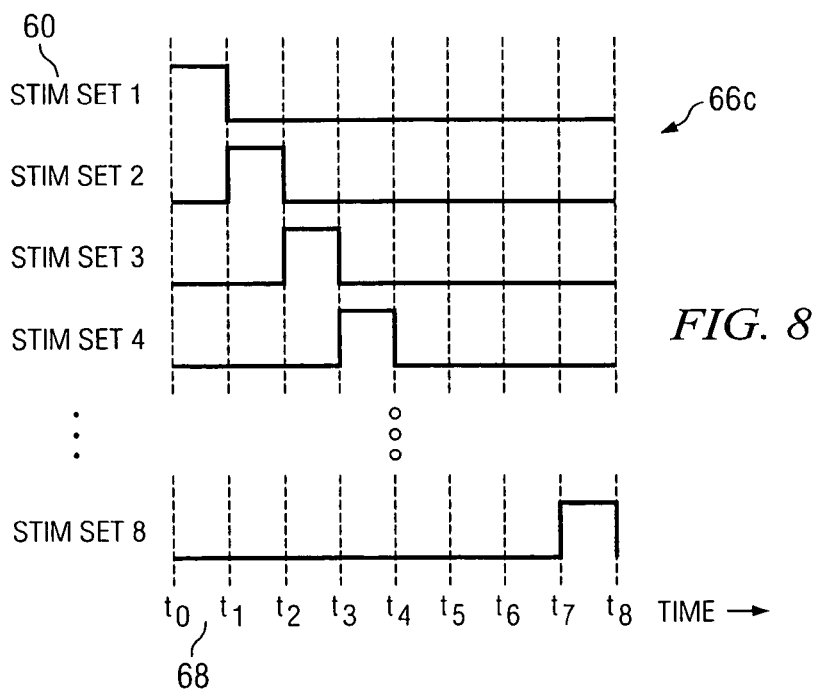
FIG. 8 illustrates example execution of a sequence of stimulation sets within an example stimulation program.
Figure 2A:
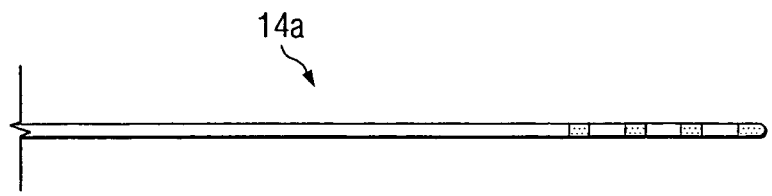
FIGS. 2A-2I illustrate example electrical stimulation leads that may be used for implantation in or near a person's brain stem for electrical stimulation of target nerve tissue in the brain stem.
Figure 2B:
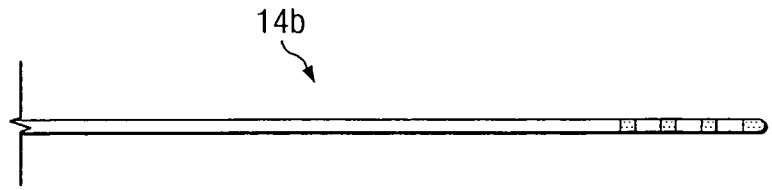
Figure 2C:
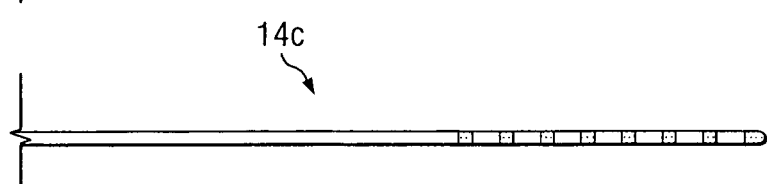
Figure 2D:
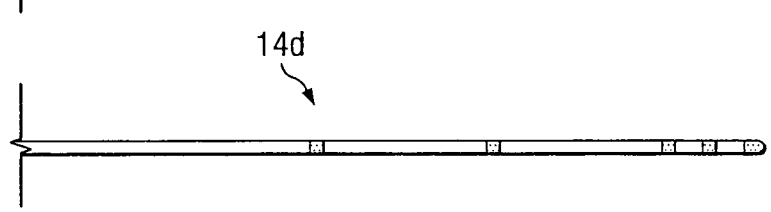
Figure 2E:
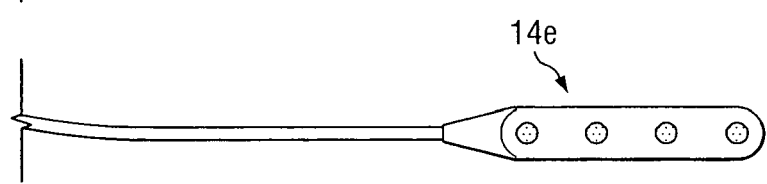
Figure 2F:
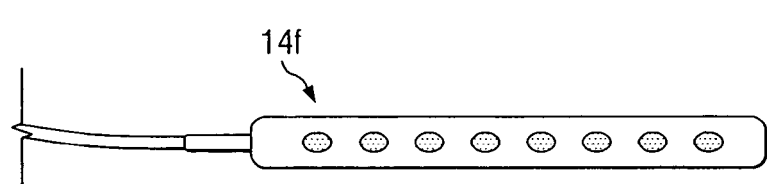
Figure 2G:
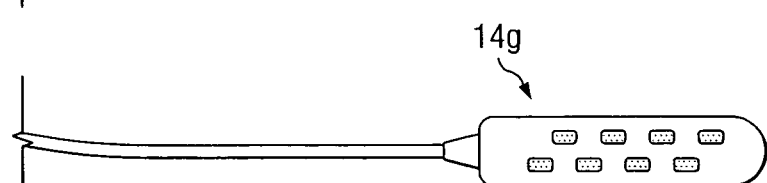
Figure 2H:
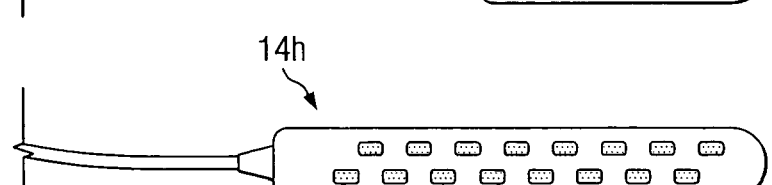
Figure 2I:
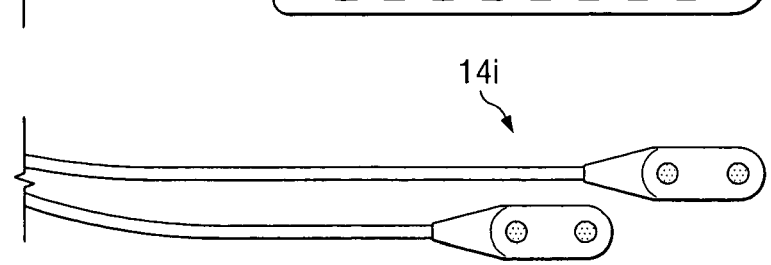
Figure 7:
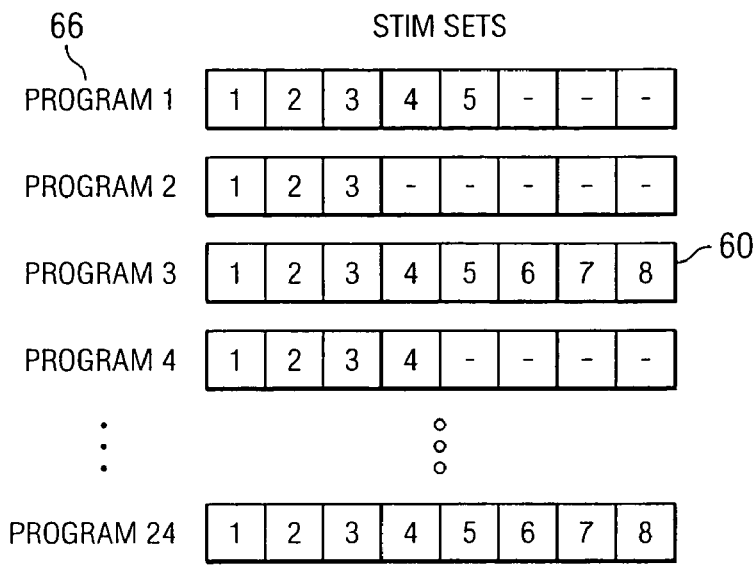
FIG. 7 illustrates a number of example stimulation programs, each of which includes a number of stimulation sets.

FIG. 7 illustrates a number of example stimulation programs 66, each including a number of stimulation sets 60. One or more simulation programs 66 may be set up to provide electrical stimulation of the brain stem. As described above, each stimulation set 60 specifies a number of stimulation parameters for the stimulation set 60. In one embodiment, within each stimulation program 66, stimulation system 10 consecutively executes the sequence of one or more stimulation sets 60 associated with stimulation program 66. The sequence may be executed only once, repeated a specified number of times, or repeated an unspecified number of times within a specified time period. For example, as is illustrated in FIG. 8 for the third example stimulation program 66c including eight stimulation sets 60, each of the eight stimulation sets 60 is consecutively executed in sequence. Although the time intervals 68 ($t_1$-$t_0$, $t_2$-$t_1$, etc.) during which the stimulation sets 60 are executed are shown as being equal, the present invention contemplates a particular stimulation set 60 being executed over a different time interval 68 than one or more other stimulation sets 60 according to particular needs.

Although stimulation system 10 is illustrated for example as accommodating up to twenty-four stimulation programs 66 each including up to eight stimulation sets 60, the present invention contemplates any number of stimulation programs 66 each including any number of stimulation sets 60. For example, in a very simple case, a single stimulation program 66 may include a single stimulation set 60, whereas in a more complex case twenty-four stimulation programs 66 may each include eight stimulation sets 60.

In one embodiment, stimulation system 10 executes only a single stimulation program 66 in response to user selection of that stimulation program for execution. In another embodiment, during a stimulation period, stimulation system 10 executes a sequence of pre-programmed stimulation programs 66 for each lead 14 until the stimulation period ends. Depending on the length of the stimulation period and the time required to execute a sequence of stimulation programs 66, the sequence may be executed one or more times. For example, the stimulation period may be defined in terms of a predetermined number of cycles each involving a single execution of the sequence of stimulation programs 66, the sequence of stimulation programs 66 being executed until the predetermined number of cycles has been completed. As another example, the stimulation period may be defined in terms of time, the sequence of stimulation programs 66 being executed until a predetermined time interval has elapsed or the patient or another user manually ends the stimulation period. Although a sequence of stimulation programs 66 is described, a single stimulation program being executed one or more times during a stimulation period according to particular needs. Furthermore, the present invention contemplates each stimulation program 66 being executed substantially immediately after execution of a previous stimulation program 66 or after a suitable time interval has elapsed since the completion of the previous stimulation program 66.

Where stimulation system 10 includes multiple leads 14, stimulation programs 66 for one lead 14 may be executed substantially simultaneously as stimulation programs 66 for one or more other leads 14, may be alternated with stimulation programs 66 for one or more other leads 14, or may be arranged in any other suitable manner with respect to stimulation programs 66 for one or more other leads 14.

In general, each stimulation program 66 may, but need not necessarily, be set up for electrical stimulation of different target nerve tissue. As an example, for electrical stimulation of the brain stem, one or more stimulation programs 66 may be set up for therapeutic electrical stimulation of certain target brain tissue in the brain stem and one or more other stimulation programs 66 may be set up for electrical stimulation certain other target brain tissue in the brain stem.

The present invention contemplates any suitable circuitry within stimulation source 12 for generating and transmitting signals for electrical stimulation of a person's brain stem. Example circuitry that may be suitable for use is illustrated and described in U.S. Pat. No. 6,609,031 B1, which is hereby incorporated by reference herein as if fully illustrated and described herein.

An electrical stimulation lead 14 or infusion catheter 14*a* may be implanted on, in, or near the brain stem using any suitable technique. For example, brain stem stimulation may be achieved by implanting an electrical stimulation lead 14 or infusion catheter 14*a* using either a percutaneous route, through an open craniotomy, or through a burr hole formed in the skull.

Figures 9A, 9B:
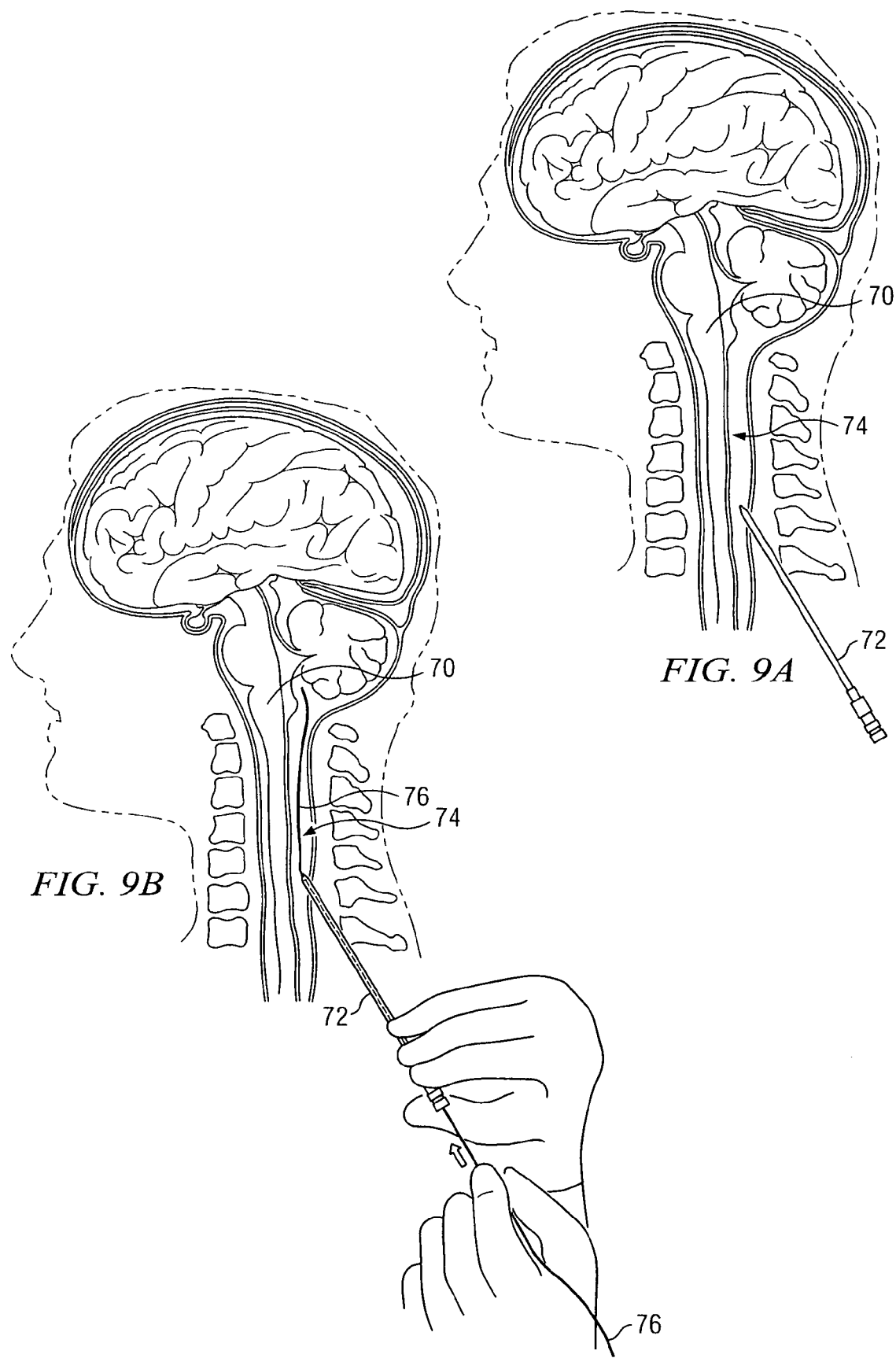
FIGS. 9A-9E illustrate an example method for percutaneous implantation of an electrical stimulation system in or near a person's brain stem.
Figure 9C:
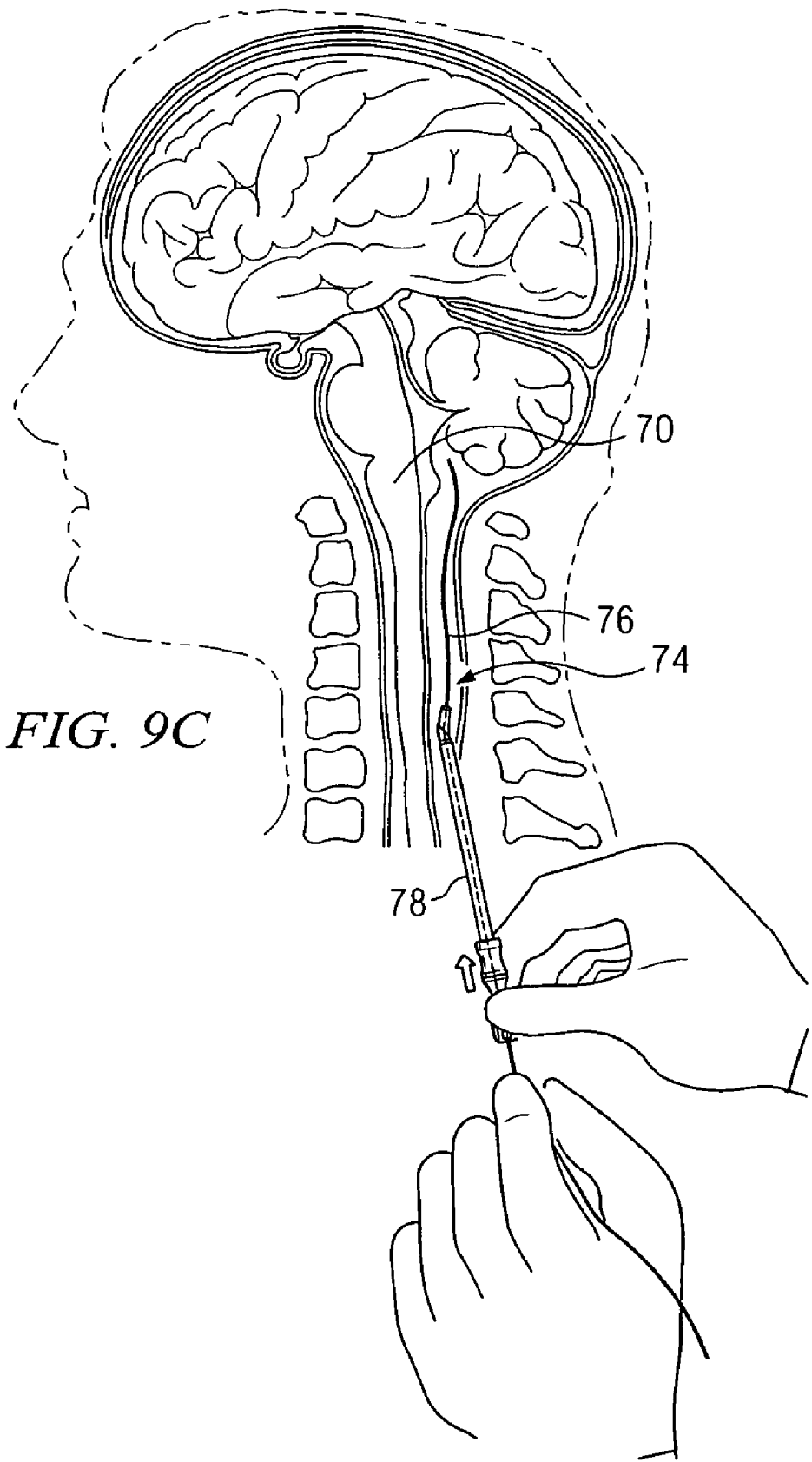

FIGS. 9A-9E illustrate an example method for percutaneous implantation of an electrical stimulation system 14 in or near a person's brain stem 70. Those skilled in the art will recognize that similar methods can be used for percutaneous implantation of infusion catheter 14*a*. In certain embodiments, as for example in the percutaneous approach, needle 72 is used to enter epidural space 74 at any vertebral level that is suitable to gain access to epidural space 74, for example, the posterior cervical or thoracic level or alternatively midline or paramedian at the level of the foramen magnum. Fluoroscopy may be used at any stage of the implantation procedure to ascertain the anatomic position of any particular device or instrumentation. The loss of resistance technique or hanging drop technique may be used to ascertain direction and depth in epidural space 74. Sterile saline or, alternatively, myelographic dye may be used to dilate epidural space 74 to facilitate passage of introducers, guide wires, electrical stimulation leads 14, and any other device that is to be introduced into epidural space 74. As shown in FIG. 9B, guide wire 76 may be inserted through needle 72 into dorsal epidural space 74 under continuous fluoroscopy to verify posterior placement in epidural space 74, lack of parathesia, the presence of cerebrospinal leak, and proper positioning of guide wire 76 in epidural space 74. As shown in FIG. 9C, after positioning guide wire 76 in epidural space 74, needle 72 may be removed and an introducer 78 may be inserted over guide wire 76 in order to avoid subsequent trauma to electrical stimulation lead 14. In alternative embodiments, electrical stimulation lead 14 may be placed through needle 72 without the use of introducer 78.

Figure 9D:
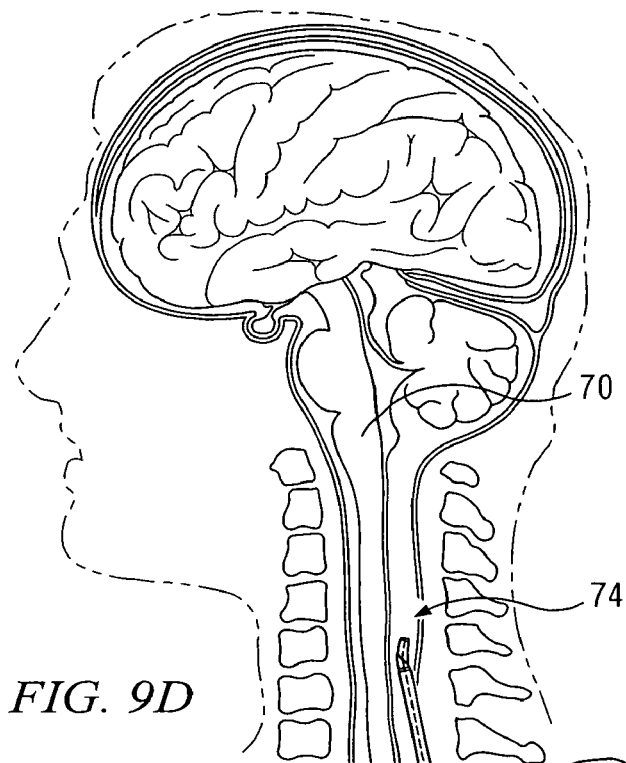
Figure 9E:
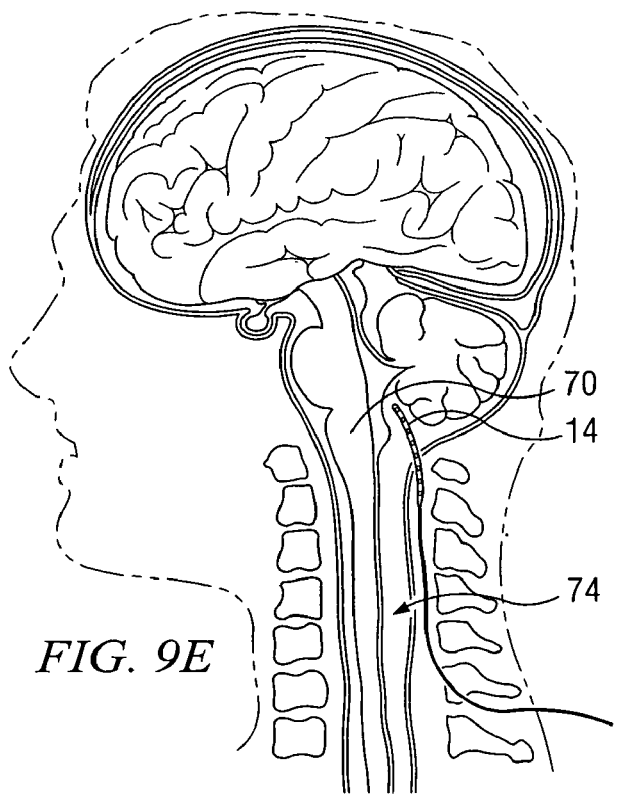

Guide wire 76 may be guided posteriorly in the midline of posterior epidural space 74 to the level of the foramen magnum, an opening at the base of a person's skull. It may be necessary to pass guide wire 76 more than once to dissect a passage under the second cervical vertebrae where epidural space 74 is narrow. Guide wire 76 may be slightly bent or curved to facilitate guidance. Alternating use of straight or bent guide wires 76 may be desired for different stages of the passage. Upon reaching the level of the foramen magnum, guide wire 76 may be used to tease open a small passage through the adhesions attaching the spinal dura to the periosteal dura, which is attached approximately at the level of the foramen magnum, thus entering epidural space 74 overlying the medulla, the lower portion of the brain stem 70. Guide wire 76 is removed and, as shown in FIG. 9D, electrical stimulation lead 14 is passed through introducer 78 and the passage created by guide wire 76. Alternatively, a relatively small "micro" electrical stimulation lead 14 may be passed directly through a hollow guide wire 76 that may be used in place of solid guide wire 76. Alternating use of straight or bent stylets, thin probes that insert into an inner channel in electrical stimulation lead 14 to straighten and stiffen it, may be used to guide electrical stimulation lead 14 along the correct path and into a desired position on, in, or near brain stem 70. As shown in FIG. 9E, electrical stimulation lead 14 is positioned at the level of epidural space 74, overlying the medulla for example, although it may be positioned on, in, or near any other structures in the brain stem to be stimulated according to particular needs.

Figure 10:
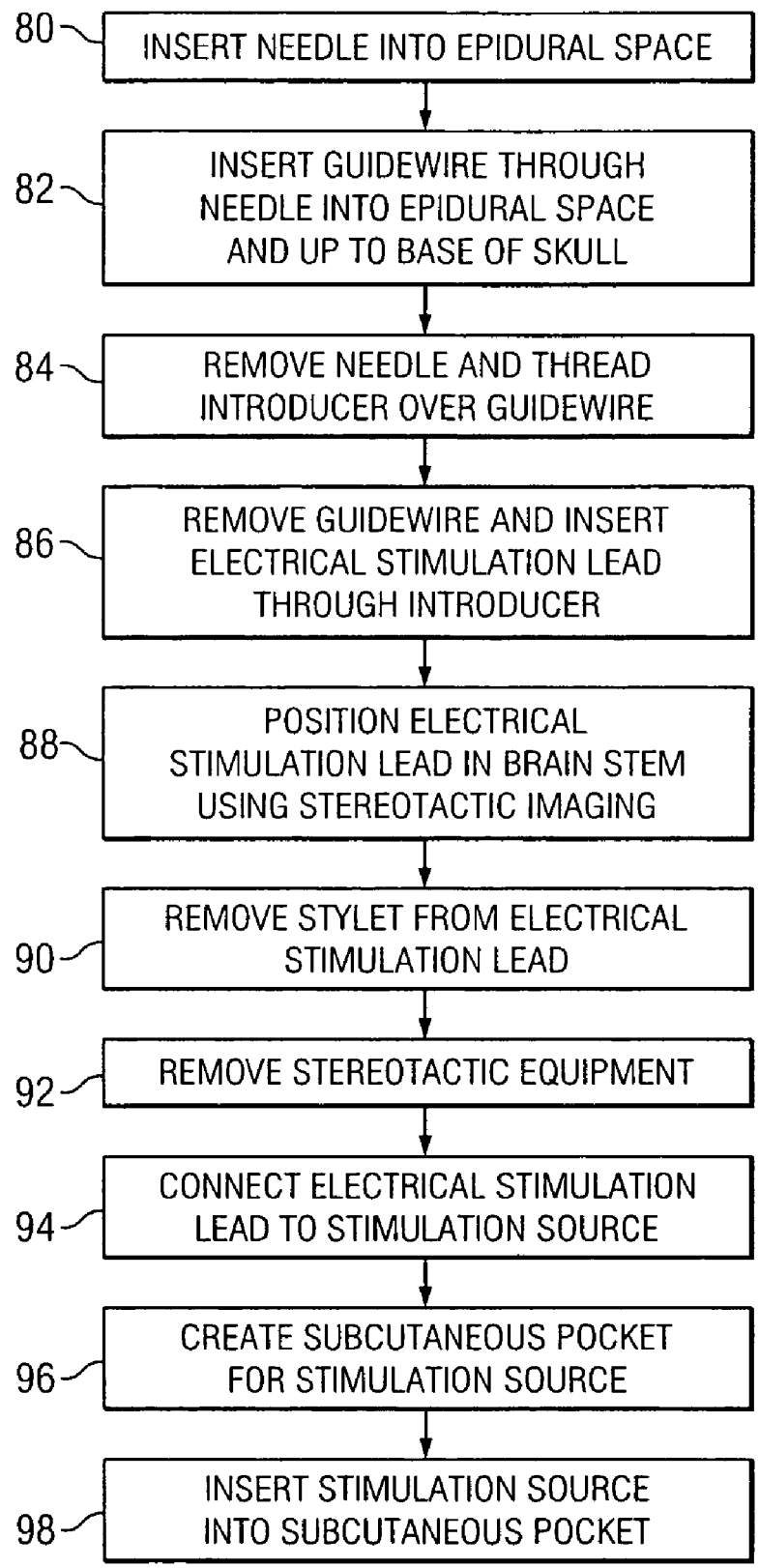
FIG. 10 illustrates steps of an example method for implanting an electrical stimulation lead in or near a person's brain stem using a percutaneous approach.

Example steps for percutaneous implantation of electrical stimulation lead 14 are shown in FIG. 10. Those skilled in the art will recognize that similar methods can be used for percutaneous implantation of infusion catheter 14*a*. At step 80, needle 72 is inserted into epidural space 74. At step 82, guide wire 76 is inserted through needle 72 into epidural space 74 and threaded up epidural space 74 to the level of the foramen magnum at the base of the skull. At step 84, needle 72 is removed and introducer 78 is threaded over guide wire 76. At step 86, guide wire 76 is removed and electrical stimulation lead 14 is inserted through introducer 78. At step 88, electrical stimulation lead 14 is positioned on, in, or near target nerve tissue to be stimulated in brain stem 70, using stereotactic imaging for example. If electrical stimulation lead 14 includes a stylet to aid in inserting lead 14, the stylet is removed at step 90. At step 92, any stereotactic equipment that may have been used to assist in placement is removed. Electrical stimulation lead is connected to stimulation source 12 at step 94, a subcutaneous pocket is created for stimulation source 12 in the chest, buttocks, or elsewhere at step 96, and stimulation source 12 is inserted into the subcutaneous pocket at step 98.

Figure 11:
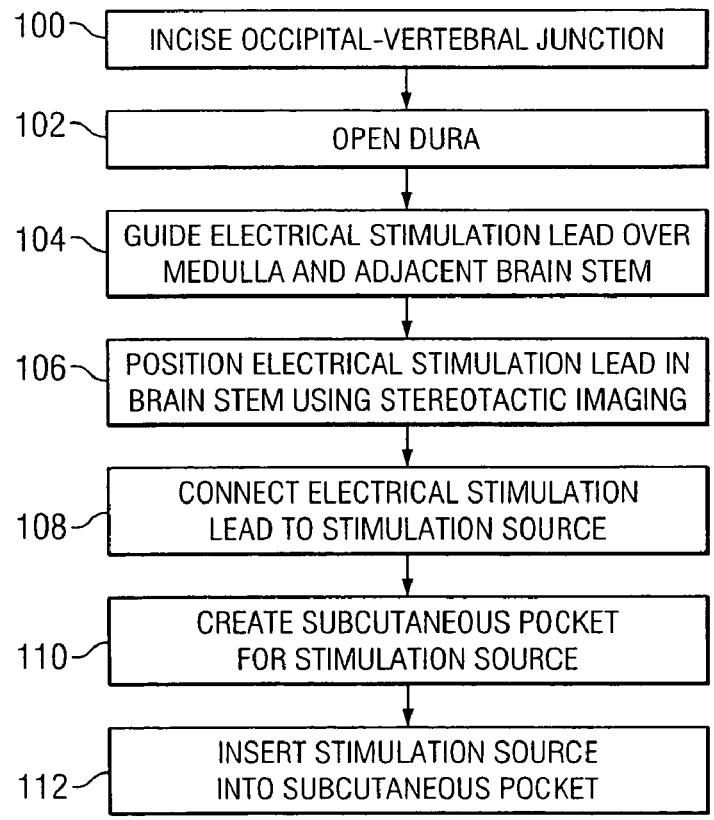
FIG. 11 illustrates steps of an example method for implanting an electrical stimulation lead in or near a person's brain stem through an open craniotomy.

In other embodiments, electrical stimulation lead 14 may be placed using an open craniotomy procedure. Those skilled in the art will recognize that similar methods can be used for the same implantation technique of infusion catheter 14*a*. FIG. 11 illustrates steps of an example method for implantation of an electrical stimulation lead 14 into a person's brain stem through an open craniotomy. At step 100, an incision may be made approximately over the junction of the occiput and the first or second cervical vertebrae, or in any other desired location to access the brain stem. The dura is opened at step 102. At step 104, electrical stimulation lead 14 may be placed under direct visualization after teasing open the dura at its attachment to the foramen magnum, directing lead 14 over the medulla portion of brain stem 70. At step 106, electrical stimulation lead 14 may be positioned more precisely using stereotactic imaging. Electrical stimulation lead is connected to stimulation source 12 at step 108, a subcutaneous pocket is created for stimulation source 12 in the chest, buttocks, or elsewhere at step 110, and stimulation source 12 is inserted into the subcutaneous pocket at step 112.

Figure 12:
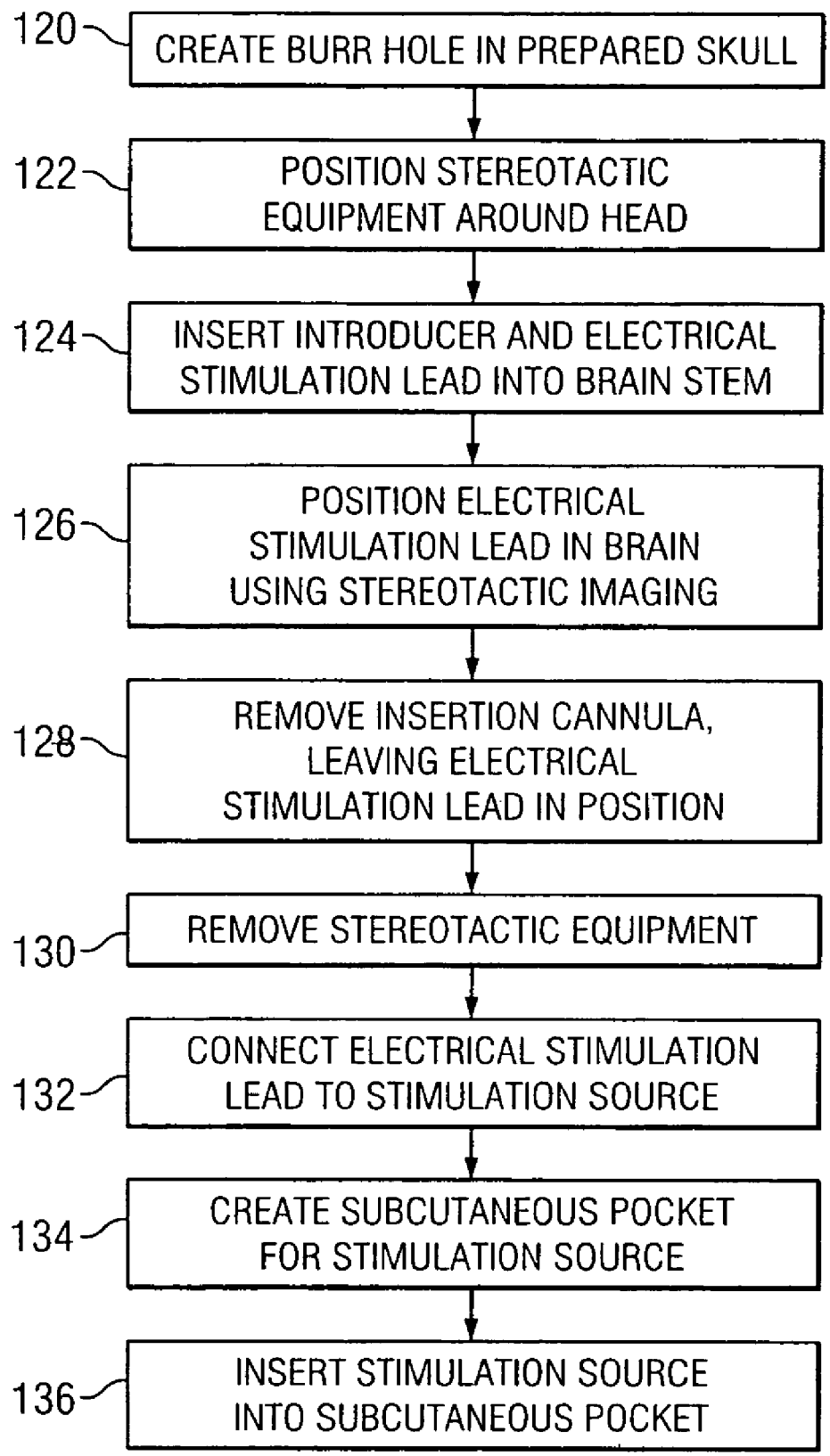
FIG. 12 illustrates steps of an example method for implanting an electrical stimulation lead in or near a person's brain stem through a burr hole formed in the skull.

In other embodiments, electrical stimulation lead 14 may be placed through a burr hole formed in the skull. Those skilled in the art will recognize that similar methods can be used for the same implantation technique of infusion catheter 14*a*. FIG. 12 illustrates steps of an example method for implantation of an electrical stimulation lead 14 into a person's brain stem through a burr hole. After the burr hole is created at step 120, an apparatus to maintain the position of electrical stimulation lead 14, a burr hole cap for example, may be seated in the burr hole. Electrical stimulation lead 14 may be directed into position using stereotactic guidance. Stereotactic equipment may be positioned around the head at step 122 if desired. At step 124, electrical stimulation lead 14 may be inserted through introducer 78 or otherwise, through a hollow guide wire 76 for example. At step 126, electrical stimulation lead 14 is positioned on, in, or near brain stem 70 using stereotactic guidance. Once electrical stimulation lead 14 has been inserted, the introducer 78, hollow guide wire 76, or other insertion cannula is removed at step 128, leaving electrical stimulation lead 14 substantially in position. At step 130, stereotactic equipment is removed. Electrical stimulation lead is connected to stimulation source 12 at step 132, a subcutaneous pocket is created for stimulation source 12 in the chest, buttocks, or elsewhere at step 134, and stimulation source 12 is inserted into the subcutaneous pocket at step 136.

The implant site is typically a subcutaneous pocket formed to receive and house stimulation source 12. The implant site is usually positioned a distance away from the insertion site, such as in the chest, buttocks, or another location. A doctor, the patient, or another user of stimulation source 12 may directly or indirectly input signal parameters for controlling the nature of the electrical stimulation provided. The various surgical approaches to implantation of an electrical stimulation lead 14, including percutaneously, through an open craniotomy, and through a burr hole, may similarly be used for implantation of an infusion catheter 14a on, in, or near the brain stem for neurological stimulation.

After successful implantation, the electrical stimulation lead 14 or infusion catheter 14a may be anchored using a variety of techniques. Standard techniques for anchoring such as suturing or the use of an adhesive may be applied to the dura. Instead or in addition, an adhesive such as benzoin, opsite, or steri-strips may be used to fix electrical stimulation lead 14 or its extension to the skin surface at the exit site of lead 14 from the body. Instead or in addition, as described more fully above, electrical stimulation lead 14 may be tunneled subcutaneously and attached to an implanted stimulation source 12.

In an alternative embodiment, a temporal approach for placement of electrical stimulation lead 14 or infusion catheter 14a may be used with or without fiber optic assistance to stimulate the trigeminal ganglion and divisions. For example, percutaneous lead placement may occur via the foramen torundum (cranial nerves II and V, the maxillary division of the trigeminal nerve, cranial nerve V) or the foramen ovale (cranial nerves III and V, the mandibular division of the trigeminal nerve, cranial nerve V) and via the sphenopalatine fossa or the sphenoid sinus respectively. A standard technique for blockade of the maxillary or mandibular nerves may be performed by injecting local anesthetic in the skin and passing an epidural needle and electrical stimulation lead 14 perpendicular to the skin under fluoroscopic guidance with the patient in the supine position and with the head turned toward the contralateral side. An epidural needle is inserted posterior to the coronoid process and under the zygomatic arch and advanced until contacting the lateral pterygoid plate. The needle is withdrawn to the subcutaneous tissue and reinserted in an anterior-superior direction approximately one centimeter deeper than the point at which the lateral pterygoid plate is contacted. Electrical stimulation lead 14 can then be threaded along the maxillary division of the trigeminal nerve. Alternatively, the needle may be inserted below the midpoint of the zygomatic arch in the mandibular notch and advanced until parathesia is reported along the mandibular nerve. Electrical stimulation lead 14 may be passed under fluoroscopy. If the lateral pterygoid plate is reached, the needle is reinserted slightly posteriorly and the process repeated. A suitable guide wire, bent or straight, may be used under fluoroscopic guidance.

Although example steps for implanting electrical stimulation lead 14 or infusion catheter 14a on, in, or near the brain stem are illustrated and described, the present invention contemplates two or more steps taking place substantially simultaneously or in a different order. In addition, the present invention contemplates using methods with additional steps, fewer steps, or different steps, so long as the steps remain appropriate for implanting electrical stimulation lead 14 or infusion catheter 14a for neurological stimulation of target nerve tissue in the brain stem.

In certain embodiments, the present invention provides electrical stimulation leads 14 having multiple electrodes 18 available in a variety of geometrical shapes that include lines, squares, circles, two-dimensional spirals, three-dimensional spirals, or other shapes known to those skilled in the art, which may be used to place and shape lead 14 as shown in FIGS. 13A-15H.

FIGS. 13A-13B illustrate an example spiral matrix electrical stimulation lead 14. Electrical stimulation lead includes a number of electrodes 18 along its length. Although electrical stimulation lead 14 is shown for example as including eight electrodes 18, lead 14 may include any appropriate number of electrodes 18 according to particular needs. In one embodiment, as shown in FIG. 13A, electrical stimulation lead 14 is formed of a resilient material and has a spiral natural position in which an array of electrodes 14 may be spaced in a matrix-like fashion over an area to be stimulated. As shown in FIG. 13B, electrical stimulation lead 14 may be straightened, for example, when a stylet is inserted in an inner channel of lead 14. When the stylet is removed, electrical stimulation lead 14 again curls into its spiral natural position as shown in FIG. 13A. Although electrical simulation lead 14 is of course three-dimensional, lead 14 may be referred to if appropriate as a "two-dimensional" lead 14 because it has a substantially planar rather than linear shape when in its spiral natural position. This type of electrical stimulation lead 14 may aid in the direct placement of electrodes 18 over the desired area. For example, once electrical stimulation lead 14 is in place, the programmer may choose the particular electrode 18 or combination of electrodes to stimulate a particular location in the brain stem.

In certain embodiments, as discussed above, electrical stimulation lead 14 may include a stylet that maintains lead 14 in a straightened position during insertion as shown in FIG. 13B. The straightened position facilitates passage of electrical stimulation lead 14 through epidural space 74. Once electrical stimulation lead 14 is properly positioned on, in, or near the brain stem, the stylet is removed and lead 14 may then curl back into its spiral natural shape as shown in FIG. 13A. Once electrical stimulation lead 14 has returned to its natural spiral position, its "two-dimensional" nature allows for an array of electrodes 18 to be situated in matrix-like fashion on, in, or near target nerve tissue in the brain stem and may allow stimulation of a broader area than would be possible using a conventional "in-line" lead. In addition, the resilient "two-dimensional" nature of electrical stimulation lead 14 helps anchor lead 14 to prevent migration or movement of lead 14 from its desired location once implanted.

Although a spiral shape is primarily described, electrical stimulation lead 14 may have any suitable substantially planar shape according to particular needs. As another example, certain embodiments may use a sheet matrix electrical stimulation lead 14 having a sheet-like natural position, adapted to be rolled upon itself similar to a scroll for insertion to a desired position on, in, or near the brain stem, through an introducer 78 or hollow guide wire 76 for example, and adapted to unroll to its sheet-like natural position after insertion. Like the spiral matrix electrical stimulation lead 14 discussed above, this may allow stimulation of a broader area than would be possible using a conventional "in-line" lead.

FIG. 14 illustrates an example "three-dimensional" electrical stimulation situated in the dural layer of the brain stem. Electrical simulation lead 14 may be referred to as "three-dimensional" rather than "two-dimensional" because it has one or more portions extending out of the plane of electrodes 18 adapted to press against surrounding tissue to further stabilize lead 14. For example, the spiral portion of electrical stimulation lead 14 containing electrodes 18 may assume its natural spiral shape in, above, or adjacent to the dura 140. Other portions of electrical stimulation lead 14 may extend into epidural space 74 to help stabilize lead 14.

Figure 15A:
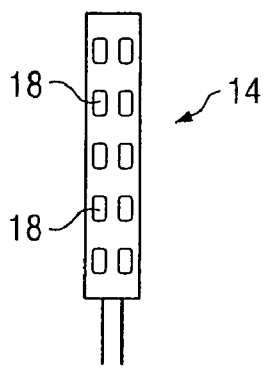
FIGS. 15A-15H illustrate other example electrical stimulation leads.
Figure 15B:
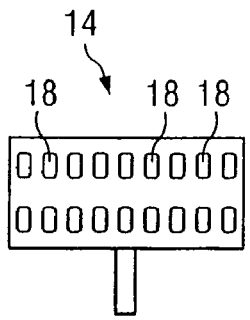
Figure 15C:
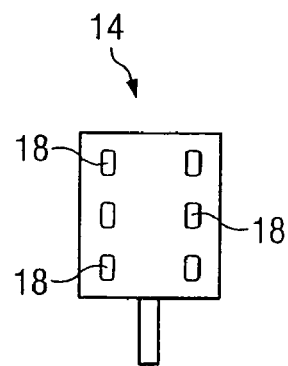
Figure 15D:
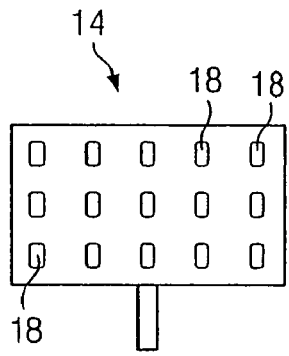
Figure 15E:
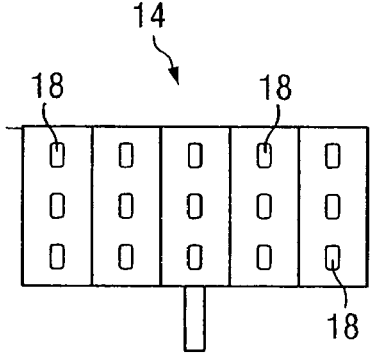
Figure 15F:
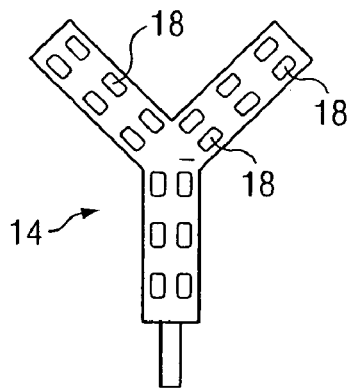
Figure 15G:
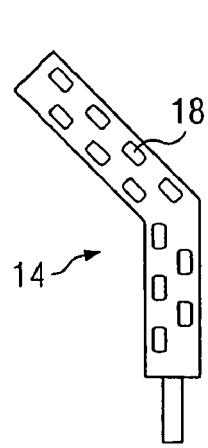
Figure 15H:
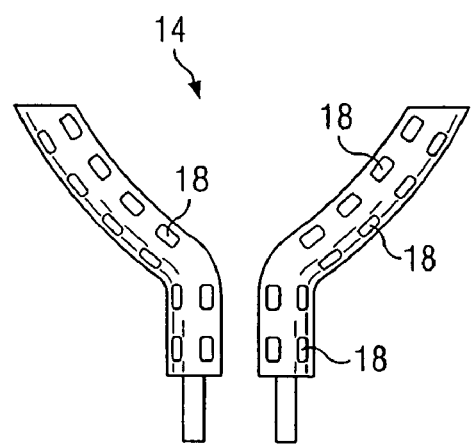

FIGS. 15A-15H illustrate other examples of configurations for electrical stimulation lead 14. Electrical stimulation lead 14 may be configured to situate in a particular anatomic region of the brain stem. The number, spacing and location of electrodes 18 on electrical stimulation lead 14 may vary according to anatomic location and electrical stimulation considerations. Certain embodiments of electrical stimulation lead 14 may allow stimulation of multiple sites on, in, or near the brain stem. Certain embodiments of electrical stimulation lead 14, such as the "T-type" lead 14 shown in FIG. 15B, may be configured to effect stimulation across the width of the brain stem over the nucleus and tractus cuneatus and the nucleus and tractus gracilis as well as the trigeminal nuclei and tracts. Certain embodiments of electrical stimulation lead 14, such as the "Y-type" lead 14 shown in FIG. 15F, may be configured to fit the area around the fourth ventricle. Certain embodiments of electrical stimulation lead 14, such as the "mirror image" leads shown in FIGS. 15G-5H, provide a matched pair of leads 14 that are mirror images of each other and may be used to provide symmetrical electrical stimulation to bilateral structures of the brain stem. FIG. 15G illustrates a "hockey stick" electrical stimulation lead 14, which fits one side of the medulla lateral to the fourth ventricle. Both left and right hand models are possible. FIG. 15H illustrates another "hockey stick" electrical stimulation lead 14, with both lateral and ventral electrodes 18 for stimulation of the lateral and ventral brain stem structures.

Figure 16A:
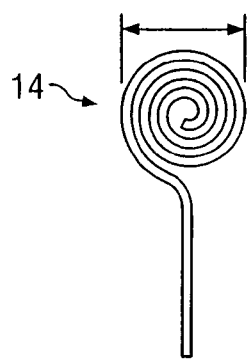
FIG. 16A-16C illustrates the coiling features of an example electrical stimulation lead.
Figure 16B:
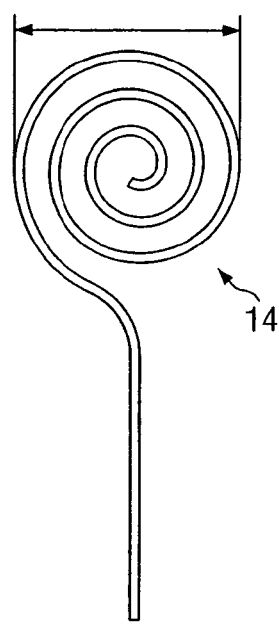
Figure 16C:
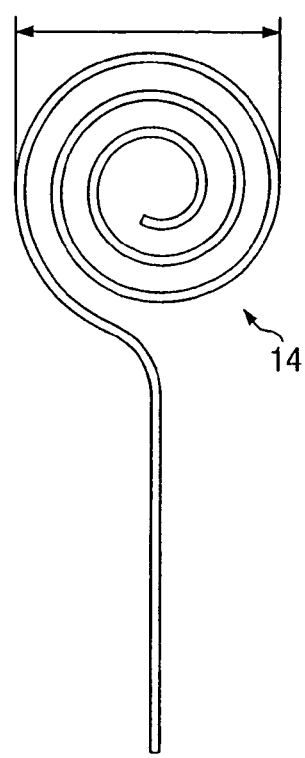

FIG. 16A-16C illustrates the coiling features of certain embodiments of electrical stimulation lead 14. In FIG. 16A, electrical stimulation lead 14 is tightly coiled because of the configuration of a stylet inserted into an inner channel of lead 14. FIG. 16B illustrates electrical stimulation lead 14 more loosely coiled, with a larger diameter, because the stylet is not as tightly coiled as in FIG. 16A. FIG. 16C illustrates electrical stimulation lead 14 even more loosely coiled, with an even larger diameter, because the stylet is not as tightly coiled as in FIG. 16B or has been removed entirely.

As described above, in certain embodiments electrical stimulation leads 14 may be implanted through an open craniotomy or burr hole formed in the skull. In these embodiments, because the brain stem may be readily accessed through the open craniotomy or burr hole, there is no need to traverse the narrow epidural channel. Accordingly, these embodiments may be most appropriate for electrical stimulation leads 14, such as those described above with reference to FIGS. 15-16, which may be placed and positioned through these larger openings in the skull.

Figure 17A:
FIGS. 17A-17B illustrate example guide wires for inserting an electrical stimulation leads.
Figure 17B:
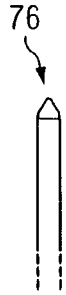
Figure 18A:
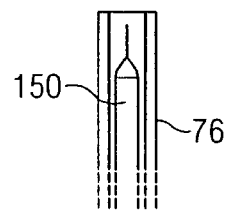
FIGS. 18A-18B illustrate an example hollow guide wire with a retractable blade for inserting an electrical stimulation lead.
Figure 18B:
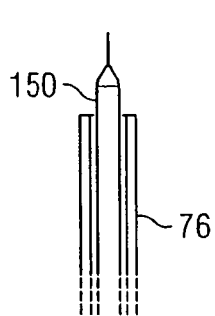

In certain embodiments, as describe above, a guide wire 76 may be used to guide electrical stimulation lead 14 into position on, in, or near target nerve tissue in the brain stem. FIGS. 17-20 illustrate example guide wires 76 that may be used in connection with insertion of an electrical stimulation lead 14. Guide wire 76 may be blunt as shown in FIG. 17A or tapered as shown in FIG. 17B. FIGS. 18A and 18B show a hollow guide wire 76 that includes a retractable blade 150, shown in a retracted position in FIG. 18A and an extended position in FIG. 18B. Retractable blade 150 in hollow guide wire 76 may be useful for dissecting through dural tissue at the level of the foramen magnum during passage of the guide wire 76.

Figure 19A:
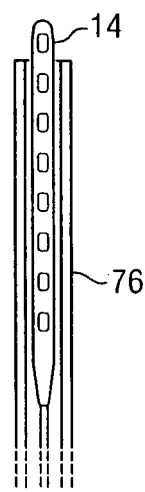
FIGS. 19A illustrates an example hollow guide wires for inserting a micro electrical stimulation lead.
Figure 19B:
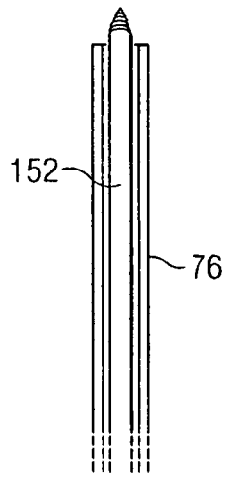
FIGS. 19B illustrates an example hollow guide wires through which a corkscrew probe may be passed.

FIG. 19A illustrates hollow guide wire 76 through which a small diameter "micro" electrical stimulation lead 14 may be passed. In certain embodiments, the present invention provides finer stimulation control as well as simplified operative placement compared to previously available electrical stimulation leads 14, because of the unique design of hollow guide 76 wire in combination with micro electrical stimulation lead 14. FIG. 19B illustrates a hollow guide wire 76 through which a corkscrew probe 152 may be passed. Corkscrew probe 152 may be used to dissect through dural tissue present at the level of the foramen magnum or any other site where dural tissue or adhesions of other origin are obstructing passage of a guide wire 76 or electrical stimulation lead.

Figure 20:
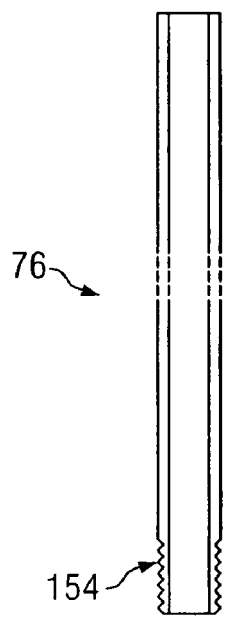
FIG. 20 illustrates an example hollow guide wire with a threaded portion configured to attach to a syringe.

Hollow guide wire 76 illustrated in FIG. 20 includes threaded portion 154 configured to attach to a syringe, for example a luer lock syringe. Attachment of a syringe to hollow guide wire 76 allows injection of solutions, such as dye, saline, or medications for example, that may assist in passage of hollow guide wire 76.

Figure 21A:
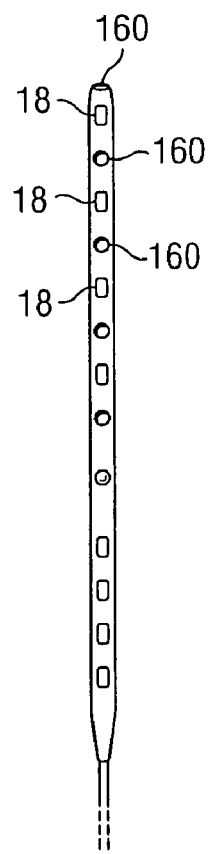
FIG. 21A illustrates an example spiral matrix electrical stimulation lead in a straightened position for insertion through an example introducer.
Figure 21B:
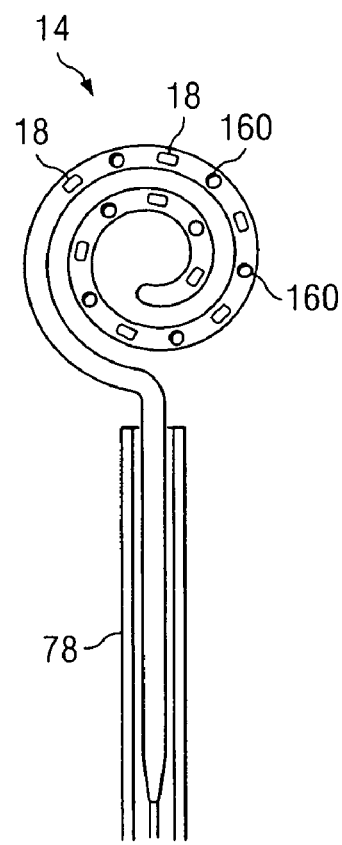
FIG. 21B illustrates an example spiral matrix electrical stimulation lead in its spiral natural position after insertion inserted through an example introducer.

In certain embodiments, an electrical stimulation lead 14 may also be used to infuse medications or other solutions into target nerve tissue in the brain stem. For example, FIGS. 21A-21B illustrate an example electrical stimulation lead 14 that includes both electrodes 18 and infusion ports 160 through which medications and other solutions may be delivered into epidural space 74 or to the targeted brain stem tissue. Electrical stimulation lead 14 may include one or more ports 160 on its side, at its tip, or both through which medications or other solutions are infused. Electrical stimulation lead 14 includes an inner channel through which medications or other solutions are delivered to ports 160. In a particular embodiment, electrical stimulation lead 14 may include side infusion ports 160 alternately situated with electrodes 18 along the length of the stimulating portion 20 of lead. In certain embodiments, an infusion catheter 14a that does not include electrodes 18 may be implanted with or without implantation of an electrical stimulation lead 14. For perioperative use, an electrical stimulation lead 14 with both electrodes 18 and ports 160 may allow for infusion initially and electrical stimulation later. Electrical stimulation leads 14 such as illustrated in FIGS. 21A-21B may also be used in central and peripheral nerve stimulation and infusion. Temporary and permanent versions of electrical stimulation leads 14 that provide for infusion and of infusion catheters 14a are possible. Long-term (e.g., up to one month) tunneled electrical stimulation leads 14 or catheters 14a can be used for perioperative pain treatment.

FIGS. 22A-22D illustrates various examples of "two-dimensional" matrix electrical stimulation leads 14. For example, particular electrode arrays allow for stimulation in a substantially two by four electrode array as shown in FIG. 22A, a substantially three by four electrode array as shown in FIG. 22B, a substantially in-line eight electrode array as shown in FIG. 22C, and a substantially three by five electrode array as shown in FIG. 22D.

In certain embodiments, a flexible electrical stimulation lead 14 may include two or more electrodes that can be wrapped around a nerve root, ganglion, or nerve structure in the brain stem. A variable "collar" can thus be readily tailored to fit a particular clinical and anatomical situation. Such an electrical stimulation lead 14, which may be similar in appearance to a standard percutaneous lead 14, provides increased flexibility and thus can be wrapped around or corkscrewed around various nervous structures.

Figure 23A:
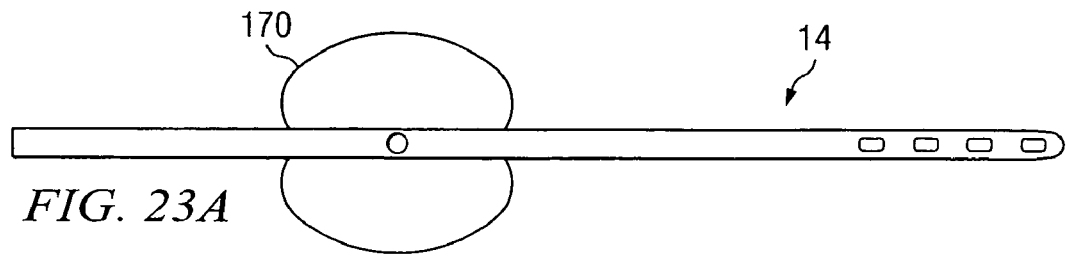
FIGS. 23A-23D illustrate example anchoring devices attached to electrical stimulation leads.
Figure 23B:
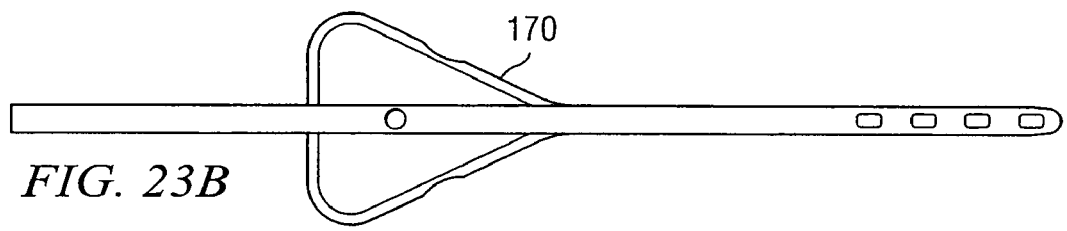
Figure 23C:
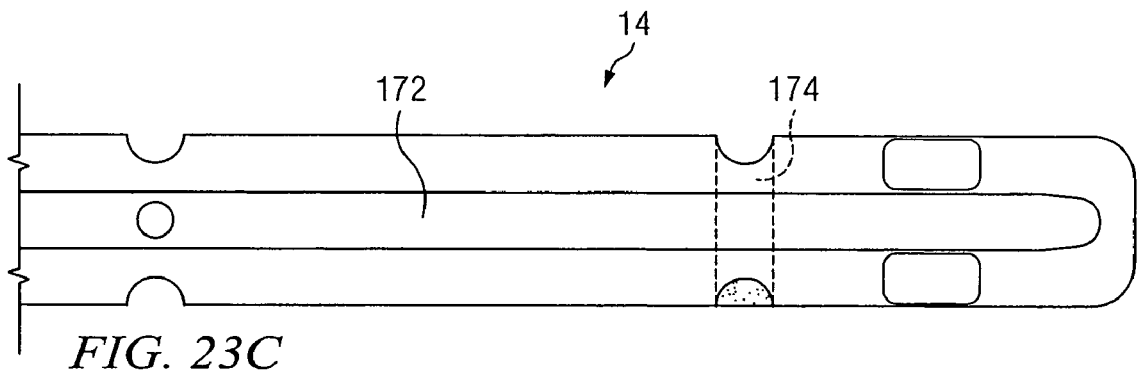
Figure 23D:
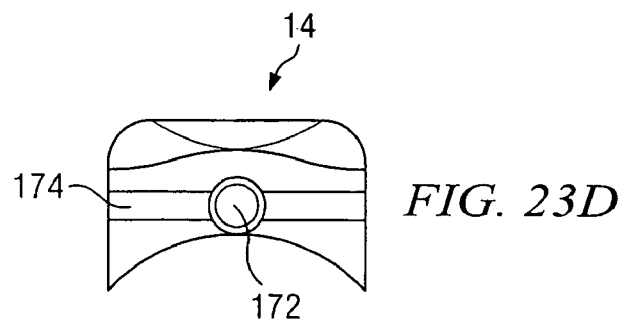

In certain embodiments, the present invention provides an improved method of anchoring an electrical stimulation lead 14 on, in, or near the brain stem using, for example, the embodiments illustrated in FIGS. 23A-23D. FIGS. 23A-23D illustrate example anchoring devices attached to electrical stimulation leads 14. In one embodiment, as shown in FIGS. 23A-23B, one or more round, tapered, or other balloons 170 may be attached to electrical stimulation lead 14 to hold lead 14 in a desired position. In another embodiment, instead or in addition, one or more pins or barbs may extend from electrical stimulation lead 14 to help prevent horizontal or vertical movement. In another embodiment, instead or in addition, a glue-like or tacky substance may be inserted through an inner channel 172 that runs the length of electrical stimulation lead 14 as shown in FIGS. 23C-23D. Channel 172 may intersect with a cross-channel 174 through which adhesive may be delivered to tissue or surrounding structures to help anchor electrical stimulation lead 14 and prevent its migration out of the desired position. Suitable adhesives may include cyanoacrylates, biocompatible glues, or other adhesives known to those skilled in the art.

Figure 24A:
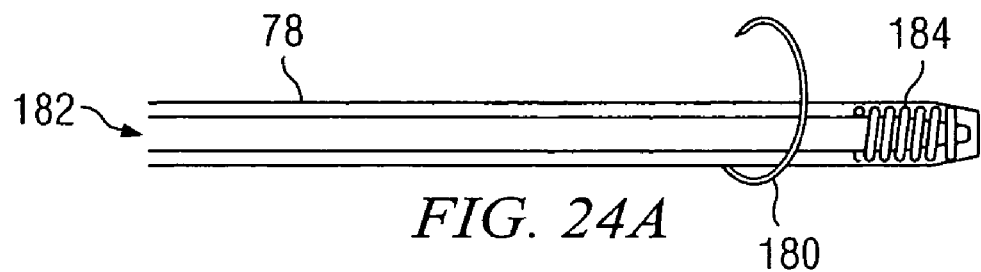
FIGS. 24A-24B illustrate an example introducers that includes a needle for fixation of the introducer during insertion of an electrical stimulation lead.
Figure 24B:
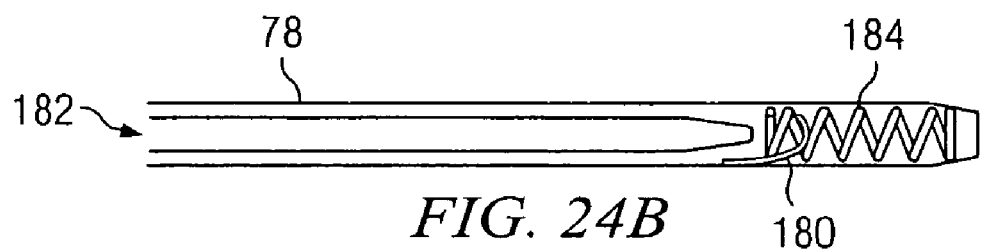

FIGS. 24A-24B illustrate an example introducer 78 that includes a needle 180 attached to its side. Needle 180 is deployed when stylet 182 compresses spring 184. Needle 180 may aid in fixation of introducer 78 during insertion of an electrical stimulation lead 14 or catheter 14a or may aid in fixation of lead 14 or catheter 14a after positioning. Although needle 180 is attached to introducer 78 in this example, it may be attached to any device introduced into epidural space 74 including a guide wire 76, and electrical stimulation lead 14, or a catheter 14a.

Figure 25A:
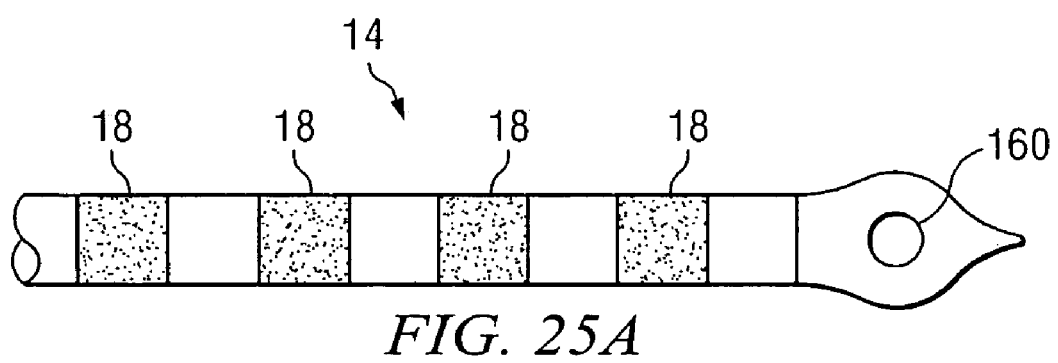
FIGS. 25A-25B illustrate an example tapered electrical stimulation lead that includes both electrodes and an infusion port.
Figure 25B:
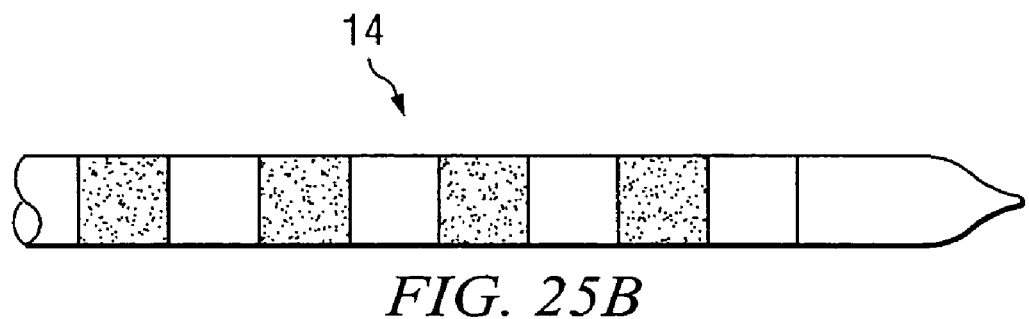

FIGS. 25A-25B illustrate an example tapered electrical stimulation lead 14 that includes both electrodes 18 and an infusion port 160. FIGS. 25A and 25B show tope and side views, respectively, of electrical stimulation lead 14. The tapered end of electrical stimulation lead 14 aids in dissection under the dura at the level of the foramen magnum.

In certain embodiments, an electrical stimulation lead 14 includes a dural cover. Such an electrical stimulation lead 14 may be used in the subarachnoid space or directly over a nerve (peripheral or central). The dural cover may be electrically identical in its properties (e.g., resistance, conductivity, impedance, etc.) to the single layer of dura and cerebrospinal fluid surrounding the spinal cord. Thus, the dural cover enables stimulation to be utilized successfully in the subarachnoid space and peripherally.

In certain embodiments, the present invention may provide smaller electrical stimulation leads 14 and electrodes 18, for example "micro" leads 14, than currently available in order to stimulate numerous sites within the brain stem. The compact nature of the brain stem, and the presence of upper limb, lower limb, trunk, and facial nerve fibers in near proximity has prevented larger electrical stimulation leads 14 from providing the fine stimulation made possible by the present invention. In certain embodiments, electrical stimulation leads 14 may be introduced using a 14-gauge modified epidural needle. In other embodiments, a 16-gauge hollow guide wire 76 may be used, through which specialized boring guides, small electrode electrical stimulation leads 14, or dye or other liquids may be injected. Any suitable sized needle, guide wire 76, introducer 78, or other device be used.

In certain embodiments, the electrical stimulation leads 14, infusion catheters 14a, guide wires 76, introducers 78, and other devices described herein facilitate stimulation of brain stem structures and fibers including but not limited to the trigeminal nucleus, nucleus and tractus gracilis and cuneatus, arcuate fibers, vagal nuclei, the vagal entry zone, nucleus and tractus solitarius, medial lemniscus, corticospinal tracts, nucleus ambiguus, cerebellar tracts, trigeminal nerves, the spinothalamic tracts, the overlying cerebellum, and any other structures in the brain stem or surrounding brain structures.

In certain embodiments, the present invention may be used to treat headache, depression, cardiac respiratory disorders, migraine headache, cluster headache, atypical facial pain, trigeminal neuralgia, occipital neuralgia, occipital headache, pseudotumor cerebri, nausea, head and neck pain, facial pain, sinus headache, upper extremity pain, lower extremity pain, trunk pain, groin pain, neck and back pain, reflex sympathetic dystrophy and causalgia of the head, neck, trunk and extremities, peripheral nerve injury, chronic regional pain syndromes, peripheral vascular disease, ischemic pain, ataxia, Parkinson's disease, movement disorders, tremor, akinesia, rigidity, dyskinesia, bladder dysfunction; detrusor dyssynergia, plexopathies, urge incontinence, interstitial cystitis, depression, seizures, thalamic pain, postsurgical pain, neuropathic pain and neuropathies, peripheral neuropathies, failed back surgery syndrome, radiculopathy, diabetic neuropathy, Raynaud's disease and syndrome, Wegener's; cancer and cancer pain, sexual dysfunction, paraplegia; spinal cord injuries, pelvic floor dysfunction, angina, obesity, anorexia, neurological disease, and spasticity.

In certain embodiments, the present invention provides a method for stimulating brain stem nuclei to treat various neurological disorders including pain. Electrodes are placed in the epidural space adjacent the targeted brain tissue to be stimulated in the brain stem. Electrical stimulation is then delivered to the nuclei resulting in stimulation of the painful region of the body or other site of desired clinical effect. Some example nuclei that may be stimulated include the gracile, cuneate and trigeminal nuclei. Stimulation of these nuclei have the potential of providing paresthesia to any area of the body. In particular, trigeminal pain has historically been difficult to treat with spinal cord stimulation. Many physicians have attempted to access the trigeminal nuclei by directly stimulating the trigeminal nerve in the periphery of the body. In certain embodiments, the present invention provides paresthesia coverage to any part of the body, including the face, through direct stimulation of brain stem nuclei.

In certain embodiments, the present invention facilitates the infusion of medications, chemotherapeutic substances, local anesthetics, general anesthetics, gene therapies, narcotics, steroids, neurolytic solutions, analgesics, radiopharmaceuticals, and other substances into the brain stem either in the subarachnoid or epidural space. Furthermore, certain embodiments may facilitate administration of general and regional anesthesia and analgesia, for example, for use in an intensive care unit, preoperatively, intraoperatively, and postoperatively. In certain embodiments, the present invention allows for the treatment of preoperative, intraoperative and postoperative pain by electrical stimulation, infusion, or a combination of the two. For example, this might include somatic perioperative pain relief by infusion, coupled with longer term neuropathic pain relief by electrical stimulation using the same combination lead/catheter, in cases of limb amputation.

Although the present invention has been described above in connection with several embodiments, a number of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A method for electrical stimulation of target nerve tissue in a person's brain stem, comprising:

selecting an electrical stimulation lead suited for implantation posteriorly on, in, or near the brain stem overlying the medulla for electrical stimulation of target nerve tissue in the brain stem, the lead comprising a plurality of electrodes adapted to be positioned posteriorly on, in, or near the brain stem overlying the medulla and to deliver electrical stimulation energy to the target nerve tissue in the brain stem, the stimulation lead having a generally spiral natural configuration, the spiral natural configuration comprising multiple turns, spacings between adjacent electrodes of the plurality of electrodes being varied between respective turns of the spiral natural configuration;

creating an opening in the person's skull overlying the medulla;

inserting a guide wire into the lead;

inserting the lead, with the guide wire, through the opening in the skull overlying the medulla;

removing the guide wire from the lead; and positioning the lead posteriorly on, in, or near the brain stem overlying the medulla for electrical stimulation of the target nerve tissue in the brain stem, wherein, upon assuming its spiral natural configuration, electrodes of the stimulation lead form a generally rectangular array overlying the medulla.

2. The method of claim 1, wherein the opening in the skull comprises an open craniotomy located approximately over the junction of the occiput and the first or second cervical vertebrae.

3. The method of claim 1, wherein the opening in the skull comprises a burr hole located approximately over the junction of the occiput and the first or second cervical vertebrae.

4. The method of claim 1, wherein the lead selected is configured for implantation on, in, or near a specific location of the brain stem overlying the medulla.

5. The method of claim 1, wherein the lead is positioned using stereotactic imaging.

6. The method of claim 1, wherein the lead is positioned using a navigation system.

7. The method of claim 1, further comprising anchoring the lead in position.

8. The method of claim 7, wherein the lead is anchored using one or more of sutures, biocompatible glue, adhesive strips and mechanical tethers.

* * * * *